United States Patent [19]
Bentsen et al.

[11] Patent Number: 5,607,645
[45] Date of Patent: Mar. 4, 1997

[54] SENSOR WITH IMPROVED DRIFT STABILITY

[75] Inventors: James G. Bentsen, North St. Paul; Kenneth B. Wood, St. Paul, both of Minn.

[73] Assignee: Minnesota Mining and Manufacturing Company, St. Paul, Minn.

[21] Appl. No.: 375,304

[22] Filed: Jan. 20, 1995

Related U.S. Application Data

[62] Division of Ser. No. 160,687, Nov. 30, 1993, Pat. No. 5,403,746.

[51] Int. Cl.$^6$ .......................... G01N 33/50; G01N 31/00
[52] U.S. Cl. ........................ 422/82.07; 422/82.05; 422/82.06; 422/82.08; 73/23.21; 436/133; 436/172
[58] Field of Search ............. 422/82.05, 82.06, 422/82.07, 82.08; 252/408.1, 304, 315.1; 73/23.21; 436/68, 133, 163, 172

[56] References Cited

U.S. PATENT DOCUMENTS

| | | | |
|---|---|---|---|
| Re. 31,879 | 5/1985 | Lübbers | 436/133 |
| 4,041,932 | 8/1977 | Fostick | 128/2 G |
| 4,510,094 | 4/1985 | Drahnak | 260/429 CY |
| 4,530,879 | 7/1985 | Drahnak | 428/352 |
| 4,557,900 | 12/1985 | Heitzmann | 422/55 |
| 4,600,484 | 7/1986 | Drahnak | 204/157.74 |
| 4,640,820 | 2/1987 | Cooper | 422/68 |
| 4,824,789 | 4/1989 | Yafuso et al. | 436/68 |
| 4,833,091 | 5/1989 | Leader et al. | 436/133 |
| 4,840,485 | 6/1989 | Gratton | 356/317 |
| 4,849,172 | 7/1989 | Yafuso et al. | 422/55 |
| 4,851,195 | 7/1989 | Matthews et al. | 422/68 |
| 4,867,919 | 9/1989 | Yafuso et al. | 264/1.5 |
| 4,916,169 | 4/1990 | Boardman et al. | 522/27 |

(List continued on next page.)

FOREIGN PATENT DOCUMENTS

| | | |
|---|---|---|
| 0471861A1 | 2/1992 | European Pat. Off. |
| 0597566A1 | 5/1994 | European Pat. Off. |
| 0601816A2 | 6/1994 | European Pat. Off. |
| WO93/07483 | 4/1993 | WIPO |

OTHER PUBLICATIONS

O. S. Wolfbeis et al. *Fresenius Z. Anal. Chem.* 1983, 314, 119–124.
W. W. Miller et al. *Clin. Chem.* 1987, 33, 1538–1542.
C. L. Clark et al. *J. Extracorporeal. Technol.* 1986, 18, 185–189.
"A Fiber–Optic Sensor for $CO_2$ Measurement", Munkholm and Walt, *Talanta*, vol. 35, No. 2, pp. 109–112 (1988).
"Fiber–Optic Fluorosensor for Oxygen and Carbon Dioxide", Wolfbeis and Weis, *Anal. Chem.*, 1988, 60, pp. 2028–2030.
"Fibre–Optic Fluorescing Sensor for Ammonia", Wolfbeis and Posch, *Analytica Chimica Acta*, 185 (1986) pp. 321–327.
Richard P. Haugland, *Handbook of Fluorescent Probes and Research Chemicals*, 5th Edition, 1992, pp. 129–141.

*Primary Examiner*—Arlen Soderquist
*Attorney, Agent, or Firm*—Gary L. Griswold; Walter N. Kim; F. Andrew Ubel

[57] ABSTRACT

The present invention provides an optical fluorescence based sensor for measuring the concentration of a gas (e.g., $CO_2$ or ammonia) in a medium such as blood which has improved drift stability. In a preferred embodiment, the sensors of the present invention comprise microcompartments of an aqueous phase having a pH sensitive sensing component within a hydrophobic barrier phase. The sensors of the present invention are substantially free of partitioning species other than the analyte of interest which can migrate from one phase to the other in response to a change in pH in the aqueous phase and which substantially affect the concentration dependent signal. In an alternative embodiment, the sensors of the present invention are constructed so as to retard the migration of partitioning species, thus reducing the initial rate of drift.

24 Claims, 17 Drawing Sheets

U.S. PATENT DOCUMENTS

| | | | |
|---|---|---|---|
| 4,943,364 | 7/1990 | Koch et al. | 204/415 |
| 4,989,606 | 2/1991 | Gehrich et al. | 128/637 |
| 5,006,247 | 4/1991 | Dennison et al. | 210/500.38 |
| 5,056,520 | 10/1991 | Tomisaka et al. | 128/634 |
| 5,114,676 | 5/1992 | Leiner et al. | 422/82.06 |
| 5,204,265 | 4/1993 | Nelson et al. | 436/8 |
| 5,219,527 | 6/1993 | Hui et al. | 422/82.06 |
| 5,246,859 | 9/1993 | Nelson et al. | 436/11 |
| 5,284,775 | 2/1994 | Yafuso et al. | 436/68 |

(ILLUSTRATING CONVENTIONAL RESULTS)

(ILLUSTRATING CONVENTIONAL RESULTS)

(ILLUSTRATING CONVENTIONAL RESULTS)

(ILLUSTRATING CONVENTIONAL RESULTS)

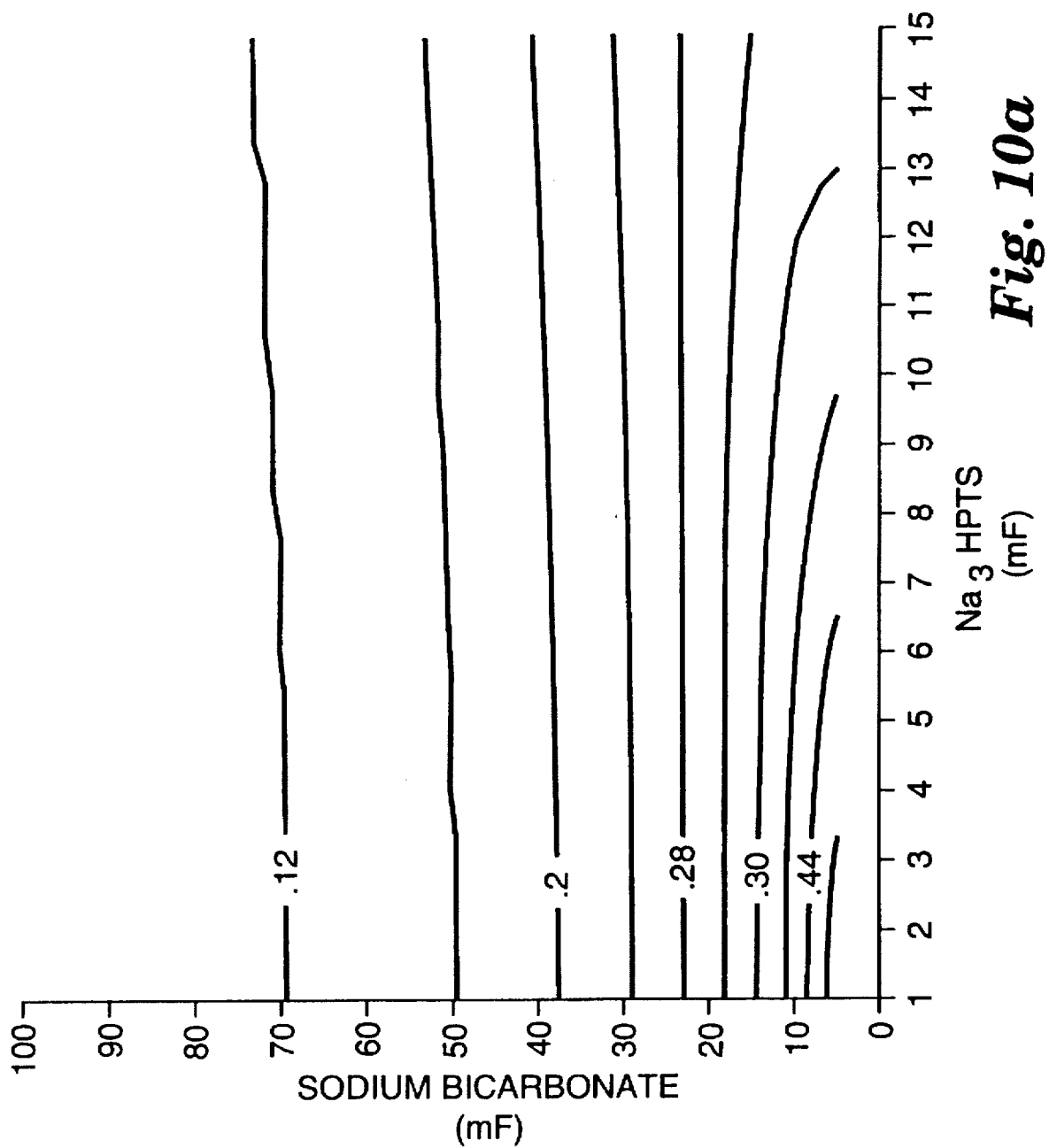

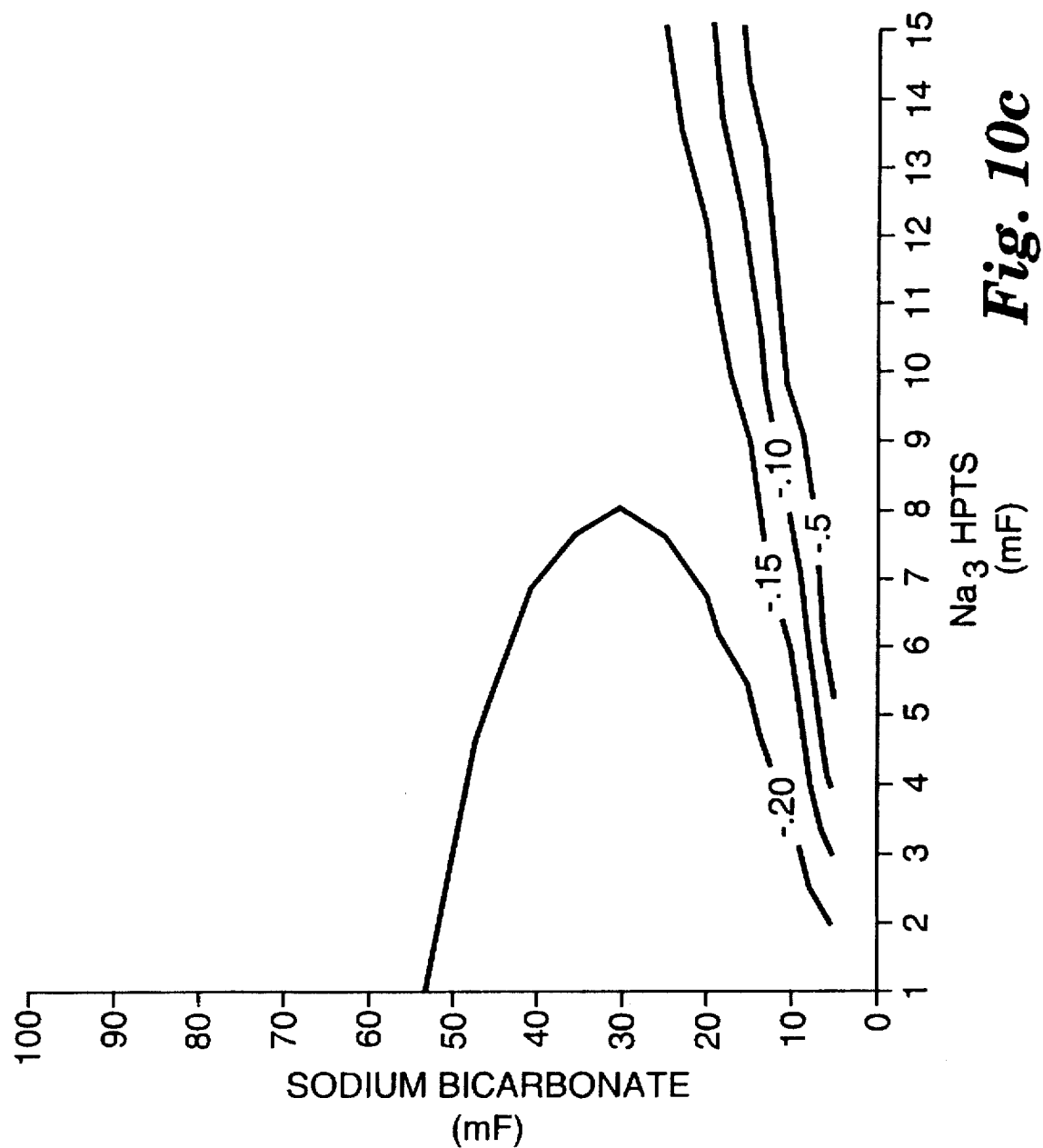

5,607,645

1

SENSOR WITH IMPROVED DRIFT STABILITY

This is a division of application Ser. No. 08/160,687 filed Nov. 30, 1993, now U.S. Pat. No. 5,403,746.

FIELD OF THE INVENTION

The present invention relates generally to sensors for measuring the concentration of an analyte of interest in a medium. In particular, the present invention includes a sensor for the monitoring of blood gas (e.g., ionized hydrogen and carbon dioxide) concentrations.

BACKGROUND OF THE INVENTION

The present invention relates to sensing or determining the concentration of an analyte of interest in a medium. More particularly, the invention relates to sensor apparatus or systems and methods for sensing the concentration of an analyte of interest, for example, carbon dioxide, in a medium, for example, blood. The invention also relates to sensor apparatus or systems and methods for sensing the concentration of an analyte of interest, for example, ammonia, $SO_2$, or $NO_2$ in industrial settings and environments.

It is sometimes necessary or desirable for a physician to determine the concentration of certain gases, e.g., oxygen, ionized hydrogen and carbon dioxide, in blood. This can be accomplished utilizing an optical sensor which contains an optical indicator responsive to the component or analyte of interest. The optical sensor is exposed to the blood, and excitation light is provided to the sensor so that the optical indicator can provide an optical signal indicative of a characteristic of the analyte of interest. For example, the optical indicator may fluoresce and provide a fluorescent optical signal as described in Lubbers et al. U.S. Pat. No. Re 31,897 or it may function on the principles of light absorbance as described, for example, in Fostick U.S. Pat. No. 4,041,932.

The use of optical fibers has been suggested as part of such sensor systems. The optical indicator is placed at the end of an optical fiber which is placed in contact with the medium to be analyzed. This approach has many advantages, particularly when it is desired to determine a concentration of analyte in a medium inside a patient's body. The optical fiber/indicator combination can be made sufficiently small in size to easily enter and remain in the cardiovascular system of the patient. Consistent and accurate concentration determinations are obtained.

Optical fluorescence $CO_2$ sensors commonly utilize an indirect method of sensing based on the hydration of $CO_2$ to carbonic acid within an optionally buffered aqueous compartment containing a pH sensitive dye. The aqueous compartment is encapsulated in a barrier material which is impermeable to hydrogen ion but permeable to $CO_2$. An optically interrogated pH change in the internal aqueous compartment can then be related to the partial pressure of $CO_2$ in the monitored sample. Ionic isolation of the internal aqueous phase may be achieved by directly dispersing aqueous droplets throughout the isolating matrix as described in U.S. Pat. No. 4,824,789 (Yafuso et al.) which is herein incorporated by reference. Alternatively, the aqueous phase may be sorbed into porous particles which are then dispersed throughout the isolating matrix as described in U.S. Pat. No. 4,557,900 (Heitzmann). The isolation matrix or "barrier" is typically a crosslinked silicone polymer. Such sensing chemistries may further comprise aqueous and silane viscosifiers and dispersing aids to stabilize the dispersion prior to crosslinking the silicone polymer.

Unfortunately, a characteristic feature of these types of sensors is reversible "$CO_2$ conditioning drift" (hereinafter for brevity sometimes referred to as "drift"), a response instability accentuated by large changes in $CO_2$ partial pressure. FIGS. 3a and 3b show typical drift data for a $CO_2$ sensor formulation in an ex-vivo blood gas sensing system. FIG. 3a illustrates a typical "intensity" plot, showing the intensity of a dye (e.g., the fluorescence intensity) as a function of time after a step change from a medium equilibrated with air ($pCO_2$=0.2 mm Hg) to a medium equilibrated with 6 volume percent $CO_2$ ($pCO_2$=45.6 mm Hg). FIG. 3b illustrates a plot of "measured" $CO_2$ concentration (calculated based on a calibration curve correlating $CO_2$ concentration or partial pressure to either dye intensity or a parameter such as a ratio of dye intensities) as a function of time after a step change from a medium equilibrated with air ($pCO_2$=0.2 mm) to a medium equilibrated with 6 volume percent $CO_2$ ($pCO_2$=45.6 mm). If a sensor in thermodynamic equilibrium with air equilibrated buffer ($pCO_2\cong0.2$ mm Hg) is suddenly exposed to an elevated $CO_2$ level such as a physiological $CO_2$ level ($pCO_2\cong45.6$ mm), the measured fluorescence intensity (illustrated in FIG. 3a) will change to a new reading within 1–2 minutes. However, when the sensor is maintained at this elevated $CO_2$ condition (e.g., $pCO_2\geq40$ mm) for several hours, the measured intensity drifts asymptotically in a direction generally opposite to the initial fast response. This is referred to as "$CO_2$ conditioning drift." The initial response to elevated $CO_2$ may be partially or completely regained if the sensor is "deconditioned" for several hours at the baseline state, therefore, the $CO_2$ conditioning effect is reversible.

This drift instability has been recognized in this type of sensor, although the specific drift mechanism has been in debate. For example, "nonspecific drift" is referred to in U.S. Pat. Nos. 5,246,859 and 4,943,364, and characterized as an instability upon exposure to low or high levels of $CO_2$. No mechanism causing this drift was postulated in these patents. One proposal put forth to explain $CO_2$ conditioning drift is outlined by Otto Wolfbeis in "Fiber Optic Chemical Sensors and Biosensors", Vol. 2, Chap. 11-V. Specifically, $CO_2$ conditioning drift is attributed to a reversible migration of water in and out of the aqueous indicator compartment, driven by a $CO_2$ dependent mismatch of the osmolarities for the aqueous indicator phase and the external medium being sensed. The $CO_2$ conditioning drift has thus been attributed to the change in the pH/$pCO_2$ relationship for the internal aqueous indicator phase as the indicator and buffer concentrations change.

Koch et al., U.S. Pat. No. 4,943,364, disclose a $CO_2$ sensor which purports to have minimal drift comprising: a hydrolyzed dye/gel polymer; optionally a solution permeable membrane; and a gas-permeable membrane. Koch et al. postulate that the cause of sensor drift in their system is due to the gradual loss of weakly bonded dye molecules from the dye/gel polymer structure. To lessen this problem Koch et al. treat their dye/gel polymer with base to remove weakly bonded dye molecules from the polymer. Unfortunately, sensors of the type described in Koch et al. are expensive to manufacture and difficult to uniformly produce.

Nelson et al., U.S. Pat. No. 5,246,859 discloses a carbon dioxide sensor and method for making carbon dioxide sensors comprising a bicarbonate buffer solution having a concentration of at least 100 mM, a hydroxy pyrene trisulfonic acid pH indicator, and a polyvinylpyrolidone aqueous phase viscosifier. The sensor may be optionally exposed to carbon dioxide gas (between 2 and 100 weight percent) prior to use. The sensor purports not to exhibit non-specific drift.

It would be desirable to provide a sensor which has a fast response time, is free of $CO_2$ conditioning drift, and is easily manufactured.

RELATED APPLICATIONS

Of related interest is U.S. Patent Application, filed on even date herewith by the assignee of this invention: "Sensing Elements and Methods for Making Same", Ser. No. 08/159,799 and copending U.S. patent applications Ser. No. 08/136,967 "Emission Quenching Sensors" and Ser. No. 08/137,289 "Sensors and Methods for Sensing" which are herein incorporated by reference.

SUMMARY OF THE INVENTION

We have discovered an optical fluorescence based sensor (e.g., for measuring $CO_2$ concentration in a medium such as blood) with improved drift stability. For sensors comprised of a pH indicator containing an aqueous phase encapsulated in a non-polar, $CO_2$ permeable barrier material, we have discovered that adventitious pH-titratable partitioning species other than the analyte of interest can reversibly migrate between the indicator and barrier phases as a function of pH, and therefore as a function of $CO_2$ partial pressure. We have also discovered that these species can also irreversibly migrate (or "leach") from the sensor to the medium. The migration of the partitioning species generates a pH response which can substantially affect the analyte concentration dependent signal. By careful choice and/or purification of sensor materials and components, we have minimized the presence of these adventitious species and developed a substantially drift-free sensor formulation. Alternatively, by proper choice of buffer composition and indicator pKa, we has discovered compositions which minimize the $CO_2$ dependent migration of adventitious species, further stabilizing these sensors.

We have made the unexpected discovery that one cause of the drift instability (commonly referred to as "analyte conditioning drift" or more specifically as "$CO_2$ conditioning drift") is actually a pH hysteresis phenomenon resulting from the presence of pH-titratable materials (hereinafter referred to as "partitioning species") which migrate in and out of the aqueous indicator phase as a function of internal pH, and therefore as a function of $CO_2$ partial pressure. While ionized species are essentially insoluble in non-polar barrier materials such as silicone, the neutral form of organic acids or bases can be very soluble in both the aqueous and silicone phases. For example, if an air equilibrated sensor comprising a sodium acetate impurity in the aqueous indicator phase is suddenly exposed to an elevated $CO_2$ level, such that the internal compartment pH drops from pH 9 to pH 7, a sudden 100 fold increase in acetic acid concentration occurs creating a thermodynamic driving force for slow migration of charge neutral acid into the silicone. Acid depletion from the aqueous indicator phase then induces additional $CO_2$ uptake and further protonation of acetate ions. This displacement of acetate by sodium bicarbonate changes the pH/pCO$_2$ relationship for the aqueous indicator phase, resulting in a slow rise in pH in opposition to the initially imposed pH drop. The migration or "partitioning" process continues until the equilibrium partitioning ratio for acetic acid is reestablished between the aqueous indicator phase and the silicone. Upon returning to the air equilibrated baseline the process is reversed. Although not recognizing the cause of the $CO_2$ drift problem, it has been a customary practice in the sensor field to package continuous blood gas monitoring sensors in a "$CO_2$ conditioned state" (i.e., at elevated $CO_2$ levels) thereby somewhat reducing excessive drift upon initial exposure to physiological $CO_2$ levels. With our new formulation, this practice should no longer be required.

A corresponding hysteresis process is operative for organic bases such as amines, since they can also migrate from the silicone phase into the aqueous indicator phase when the $CO_2$ level is elevated. For example, if an air equilibrated sensor comprising an amine impurity in the silicone phase is suddenly exposed to an elevated $CO_2$ level, such that the internal compartment pH drops from pH 9 to pH 7, a sudden 100 fold increase in ammonium ion concentration occurs creating a thermodynamic driving force for slow migration of charge neutral amine from the silicone into the aqueous phase. Amine uptake to the aqueous indicator phase then induces additional $CO_2$ uptake and further protonation of amine. This accumulation of ammonium ions changes the pH/pCO$_2$ relationship for the aqueous indicator phase, resulting in a slow rise in pH in opposition to the initially imposed pH drop. The migration or "partitioning" process continues until the equilibrium partitioning ratio for amine is reestablished. Upon returning to the air equilibrated baseline the process is reversed. Notably, the effect on the sensor response is identical for both acetate depletion and amine uptake; that is, when moved from an air equilibrated medium to a medium equilibrated at a higher $CO_2$ level, a negative mm drift will result in the presence of either type of species. This hysteresis process can also occur for the indicator dye itself if the dye exists in equilibrium with a partitionable charge neutral form.

Another cause of drift instability (referred to as "saline conditioning drift" or "saline drift") is actually a pH dependent phenomenon resulting from the presence of pH-titratable materials which migrate from the sensor to the medium (e.g., typically an aqueous buffer solution which has a pH of 9 when at air equilibrium) as a function of external pH, and therefore as a function of $CO_2$ partial pressure. For example, if an air equilibrated sensor comprising an amine impurity in the silicone is suddenly exposed to an elevated $CO_2$ level, the pH of the external buffer drops from pH 9 to pH 7, creating a driving force for slow migration of charge neutral amine from the silicone into the external aqueous medium where it becomes protonated. This process impacts the amount of amine available for partitioning into the internal aqueous compartment. Notably, the effect on the sensor response is opposite to the previously discussed $CO_2$ conditioning drift. That is to say, the sensor exhibits a positive mm drift due to these migrating species.

With this new understanding, we have developed new $CO_2$ sensor formulations which contain less than a critical amount of titratable partitioning species, and exhibit substantially drift free response. As used herein the terms "drift free" or "substantially drift free" mean that the sensor provides a signal which drifts less than 12% (i.e., <5.5 mm) over a three hour period when moved from a medium equilibrated with a gas having a pCO$_2$ of 0.25 mm to a medium equilibrated with a gas having a pCO$_2$ of 45.6 mm as herein described (see Example 1 and FIG. 3$b$ for details of this calculation). More preferably, the sensor provides a signal which drifts less than 6% when moved from a medium equilibrated with a gas having a pCO$_2$ of 0.25 mm (i.e., air equilibrated) to a medium equilibrated with a gas having a pCO$_2$ of 45.6 mm. Most preferably, the sensor provides a signal which drifts less than 3% when moved from a medium equilibrated with a gas having a $pCO_2$ of 0.25 mm to a medium equilibrated with a gas having a $pCO_2$ of 45.6 mm. This advance offers several practical advantages.

In one embodiment, the sensor is maintained in an air-equilibrated buffer condition, except during temporal physiological $CO_2$ sampling. For example, certain commercial ex-vivo sensing systems contain a sensing element (e.g., a sensor composition housed in a cassette which is attached to an optical fiber or which alternatively contains an excitation light source) in the a-line circuit of arterially catheterized patients. Blood gas levels are monitored temporally (e.g., "on demand" by the health care provider or automatically by means of a programmed pump or motor) by drawing blood up the saline drip line into the sensor cassette, and then allowing the blood to return to the patient. The present invention, when used in such a configuration, should remove earlier limitations on the frequency and duration of physiological $CO_2$ sampling that can be achieved without incurring or inducing drift.

In another embodiment, this invention provides a new and improved gas sensor of such a size so as to be capable of being introduced directly into the body of a patient as for instance by intravenous, intraarterial or interstitial introduction. The sensor may be stored in an air equilibrated buffer medium prior to use without incurring or inducing drift. The sensor can provide a "continuous" signal representative of the gas concentration over a prolonged period and over wide ranges of analyte concentration without incurring or inducing drift.

Sensors of the present invention are easily calibrated and may reside in the calibration medium before, during and after calibration without the special precautions commonly employed to limit "$CO_2$ conditioning drift" or "saline drift".

In general, the magnitude of drift exhibited by traditional sensors is proportional with the buffering capacity of the aqueous indicator compartment. Sensors of the present invention, preferably being substantially free of partitioning species, enjoy the advantage of being far less susceptible to drift even when the buffering capacity of the aqueous indicator phase is decreased. This enables design of sensors with a faster response time, without introducing a prohibitive rate and/or amount of drift. In addition, the gas sensors of the invention are stable (i.e., drift free), reproducible and tolerant of production variables without detracting from the inherent properties of the gas sensors. Alternatively, one can reduce the drift exhibited by sensors that contain small amounts of partitioning species by employing higher buffer concentrations as herein described. Finally, one may combine a higher buffer concentration with a "clean" sensor chemistry and produce a drift free sensor which is less susceptible to externally induced drift such as might be caused by exposure of the sensor to a medium which contains a partitioning species.

This can be advantageously accomplished in a gas sensor which comprises an aqueous first phase including a dye and a hydrophobic second phase, and which is substantially free of partitioning impurities which can migrate from one phase to the other in response to a change in pH in the first phase and which substantially affect the concentration dependent signal. In a preferred embodiment, the first phase comprises an aqueous buffered solvent and a dye and the second phase comprises a cross-linked polymeric material which is gas permeable, light permeable and is impermeable to liquid water and protons.

In one embodiment, the first phase comprises a dye in a hydrophilic fluid which is absorbed or adsorbed on carrier beads or particles. These beads or particles are then taken up in a matrix of a hydrophobic material. For example, an aqueous solution of a pH responsive dye (e.g., 8-hydroxypyrene-1,3,6-trisulfonic acid "HPTS") in sodium bicarbonate is absorbed into the voids of polyacrylamide particles (e.g., having a diameter of approximately 35 µm). The particles are then incorporated into a polymeric precursor which is then cured to form a disk of polymeric material (e.g., polydimethyl siloxane) which is incorporated into a cassette fixture.

In another presently preferred embodiment, the first and second phases are formed into a permanent "emulsoid" of suspended or dispersed micro-compartments of the aqueous first phase in the cross-linked polymeric second phase wherein the micro-compartments of the aqueous first phase are preferably smaller than 5 microns, and more preferably smaller than 2 microns. In yet an alternative embodiment, the first phase and second phase may be provided as a laminate.

In an illustrative embodiment of the invention, the dye is a pH sensitive dye, the aqueous buffer solvent is a physiological pH range buffer solution as for instance a bicarbonate ion based buffer solution. In this illustrative embodiment the polymeric material is a silicone material as for instance a siloxane material which is carbon dioxide permeable. More specifically the material is polydimethylsiloxane or polydimethylsiloxane copolymers. The dye in the illustrative embodiment is the trisodium salt of hydroxypyrene trisulfonic acid "HPTS").

In an illustrative embodiment of the process, the dye is present in the aqueous phase in a concentration of about 1 to about 15 millimolar and the buffer is present in the aqueous phase in a concentration of from about 1 to about 100 millimolar. More preferably, the dye and buffer are present in a concentration of from about 1 to about 10 and 1 to 50 millimolar, respectfully, and most preferably the dye and buffer are present in a concentration of from about 1 to 5 and 5 to 20 millimolar, respectfully.

A further advantageous process of preparing a gas sensor comprises dissolving a quantity of a dye in a quantity of aqueous buffer solution followed by vigorously mixing the buffer solution with a quantity of a polymeric precursor of a cross-linked polymeric material so as to form an emulsion (or suspension) of the buffer solution and the polymeric precursor. Then a quantity of a cross-linking agent and catalyst are added to the emulsion. The catalyzed emulsion is formed into a shape (e.g., a small drop at the end of an optical fiber or a sheet or disc suitable for insertion into a sensor cassette) and cured to form a permanent emulsoid (which is substantially free of partitioning species which can migrate from one phase to the other in response to a change in pH in the buffer solution and which substantially affect the analyte concentration dependent signal) of micro-compartments of the dye containing aqueous buffer solution in the cross-linked polymeric material. The above process can be augmented by adding a quantity of an emulsification enhancement agent (e.g., a thickener or surfactant) to the solution of the dye in the buffer so as to form a mixture of the dye and the emulsification enhancement agent in the buffer and/or by adding a dispersing agent such as fumed silica to the hydrophobic phase.

BRIEF DESCRIPTION OF THE DRAWINGS

This invention will be better understood when taken in conjunction with the drawings wherein:

FIGS. 10a–g are contour plots of predicted sensor performance based on a mathematical treatment of the partitioning process.

Figure 1:
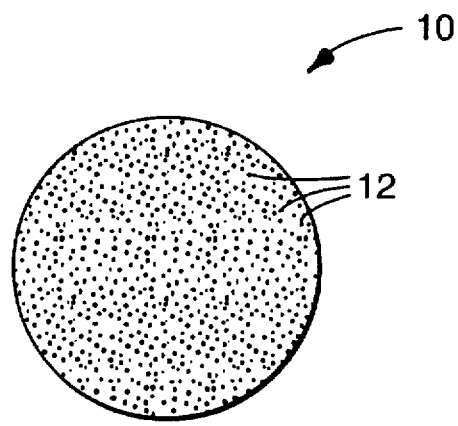
FIG. 1 is an elevational view in section of a droplet of material utilized in the preparation of a gas sensor of the invention.

This invention utilizes certain principles and/or concepts as are set forth in the claims appended to this specification. Those skilled in the gas sensing arts to which this invention pertains will realize that these principles and/or concepts are capable of being illustrated in a variety of embodiment which may differ from the exact embodiments utilized for illustrative purposes in this specification. For these reasons, the invention described in this specification is not to be construed as being limited to only the illustrative embodiments but is only to be construed in view of the appended claims.

DETAILED DESCRIPTION OF THE INVENTION

As used herein, the terms "aqueous first phase" or "aqueous phase" refer to the hydrophilic phase or phases of a multiphase sensor which comprises a pH responsive indicator component ("dye") and which more preferably, but not necessarily, further comprises water.

As used herein, the terms "hydrophobic second phase" or "hydrophobic phase" refer to that phase of a multiphase sensor which separates an aqueous phase (comprising an indicator component) from the medium containing the analyte of interest. As used herein, the terms "polymeric phase" or "silicone phase" refer to a hydrophobic second phase which comprises a polymer material or silicone material respectfully.

As used herein, the term "partitioning species" refers to those species, other than the analyte of interest, which can migrate from the aqueous phase to the hydrophobic phase (or vice versa) in response to a change in pH in the aqueous phase and which substantially affect the concentration dependent signal (i.e., the signal provided by the indicator component which is proportional to the concentration of the analyte of interest in the medium being measured). A material is "substantially free" of partitioning species when the species are no longer capable of substantially affecting the concentration dependent signal.

As used herein, the term "emulsion" refers to a uniform multi-phase system of two or more liquids and includes dispersions and suspensions. The use of the term emulsion is not limited to thermodynamically stable mixtures or mixtures containing emulsifiers. As used herein, the term "stable emulsion" refers to emulsions which remain substantially uniform (macroscopically) for long enough period of time to allow the emulsion to be formed into the desired configuration, e.g., a period of at least several hours.

As used herein, the term "emulsoid" refers to a multi-phase system comprising micro-compartments of a dispersed phase in a second solid phase (e.g., a cross-linked polymer phase).

As used herein, the term "response time" refers to the time necessary for the concentration dependent signal of a given sensor to reflect the concentration of the analyte of interest when the sensor is exposed to the medium containing the analyte. The response time includes any time necessary for the sensor to stabilize to the medium, but does not include the time over which migration of partitioning species occurs to introduce drift. Preferred sensors of the present invention have a response time less than 5 minutes, more preferably less than 2 minutes, and most preferably less than 1 minute.

As used herein, the term "purify" refers to the removal or substantial removal, from a material or article, of any partitioning species which may be present in the material or article. As used herein, the term "immobilize" refers to the fixing of a partitioning species to another species or material so as to render the partitioning species incapable of migration.

As used herein, the term "specific sensitivity" refers to the differential change in concentration of the basic form of the indicator $(I_1-I_2/I_1)$ at two partial pressures which bracket the range of interest (i.e., $I_1$ is measured when the sensor is exposed to a medium equilibrated with 2.8 volume % $CO_2$ and $I_2$ is measured when the sensor is exposed to a medium equilibrated with 8.4 volume % $CO_2$).

In one embodiment, this invention is directed to a gas sensor which can be utilized with a fiber optical cable, i.e., a single optical fiber or a bundle of the same. The fiber optic cable is associated with appropriate optical and electronic devices for imposing an optical signal from the gas sensor. A plurality of techniques for transmitting and reading appropriate optical signals can be utilized with the gas sensors of the invention. For brevity of this specification, the optics and electronics for gas sensing will not be reviewed in detail, reference being made to the above referenced patents to Lubbers et al. and Heitzmann. For these reasons the entire disclosures of U.S. Pat. No. RE 31,879 to Lubbers et al. and U.S. Pat. No. 4,557,900 to Heitzmann are herein incorporated by reference. Notably, other means of transmitting light to and from the sensor may be employed. For example, a light source such as a LED may be placed next to or against the sensor.

According to the present invention a dye or optical indicator is utilized for sensing a gas of interest. The dye can be one which acts with the gas of interest either by directly interacting with the gas or by indirectly acting with the gas, as for example, by sensing a pH change in a medium wherein the pH change is caused by interaction of the gas of interest with that medium. Interaction of the gas of interest with the dye, either directly or indirectly, can be monitored by any suitable optical technique as for instance by either fluorescence or by absorption.

In a presently preferred embodiment, a solution of a suitable indicator dye is formed in an aqueous buffer. The aqueous phase is then emulsified with (or uniformly dispersed or suspended with) a liquid precursor of a polymeric material. During the emulsification or suspension step, the aqueous phase is broken up into very small droplet sizes. The polymeric material is chosen such that the aqueous phase is not readily soluble in either the precursor materials for the polymeric material or the polymerized polymeric material. Thus the aqueous phase always retains its integrity. By emulsifying or suspending the aqueous phase into the polymeric precursor materials, very small discrete "micro-compartments" or cells of the aqueous first phase can be formed in the polymeric second phase. Upon curing or crosslinking of the polymeric phase, these micro-compartments are fixed in dispersed positions which are essentially uniformly scattered throughout the polymeric material. An "emulsoid" of the aqueous first phase is thus formed in the polymeric second phase. Since the aqueous phase in this preferred embodiment is very evenly distributed within the polymeric phase, when it is fixed in position in the emulsoid, its concentration is very evenly distributed throughout the emulsoid. Because the concentration of the aqueous phase is uniform through the emulsoid, the sensing characteristics of the gas sensor of the invention are also very uniform. Contrary to other gas sensors, by using very small emulsion sized particles, the surface area of the individual micro-compartments and thus the totality of the micro-compartments of the aqueous phase is very large. Gas exchange between the polymeric phase and the aqueous phase is across the interface between the surface of the aqueous phase and the polymeric phase. Because the surface area of the aqueous phase which is in contact with the surface area of the polymeric phase is very large, for the gas sensors of this invention, gas exchange to the sensing aqueous phase is fast and is uniformly sensitive to the gas concentration within the polymeric phase.

We have discovered that certain materials used in traditional $CO_2$ sensors, for example, in the aqueous first phase, in the hydrophobic second phase, or in other parts of the sensor, undesirably contribute to $CO_2$ conditioning drift and/or saline drift. These materials may themselves contribute to drift or contain "impurities" or residual species (hereinafter collectively referred to as "partitioning species") that contribute to the drift problem. The amount of such materials or impurities needed for drift to occur is extremely small. Because of the large number of ingredients and materials that go into a typical $CO_2$ sensor, titratable partitioning species are ubiquitous unless extraordinary precautions are taken to eliminate them or control them. Each and every part of the sensor must be considered for its potential contribution of titratable partitioning species. This includes the aqueous phase (including, for example, thickeners or viscosifiers used therein), the hydrophobic phase (including, for example, the silicone polymer and/or crosslinker, and fillers used therein), any optional films or overcoats (for example, substrate films or webs used when coating sensing elements, optical barrier films, etc.), and any optional adhesives and/or adhesion promoters used to secure the sensor to an optical fiber, cassette, or a substrate film. The partitioning species may also be liberated or released from one or more of the sensor components as a result of a subsequent process (e.g., a heating process) or exposure to an environment. For example, some materials contained within traditional sensors contain species which are believed to become partitioning species only when the sensor is steam sterilized or heated (e.g., dextran thickeners may liberate carboxylic acids and certain polyester films, used as a substrate upon which to coat the sensor, may liberate terepthalic acid). With this new understanding of the causes of $CO_2$ conditioning drift and saline drift we have also discovered several methods to provide sensors which are essentially drift free. By careful selection and/or purification of components we have developed $CO_2$ sensing chemistry, and sensing elements, which are essentially drift-free, and which are not adversely affected by steam sterilization.

We have also discovered that one can control the rate of drift by changing sensor geometry. For example, the migration of species between the aqueous phase and hydrophobic phase can be slowed by appropriate barrier means such as an asymetric nylon membrane. Likewise, appropriate coatings or barriers between the sensor and the medium can slow the migration of species from the sensor to the medium (i.e., slow the rate of "saline drift").

At a minimum, the aqueous phase must contain an indicator of the gas of interest for which the sensor is being used. Other materials can be incorporated into the aqueous phase micro-compartments subject to the limitation described herein that the other material not contribute to appreciable analyte conditioning drift or saline drift. Depending on the gas of interest, these other materials would be chosen to contribute to the operating characteristics of the gas sensor. For example, additional materials can be added to promote the emulsification or suspension of the aqueous phase into the polymeric phase. Further, they can be added to lower the vapor pressure of the aqueous phase in the polymeric phase so as to retard the evaporation of the aqueous phase during formation of the gas sensor of interest. Aside from materials which contribute to the physical formation of the emulsoid of the aqueous phase in the polymeric phase, further additives can be added to the aqueous phase for enhancement of the storage and/or operating characteristics of the gas sensor as for instance osmoregulatory agents (e.g., NaCl) and/or bacteriostatic agents.

A particular gas of interest for the gas sensor of this invention is carbon dioxide. For sensing carbon dioxide a pH sensitive dye would be solubilized in the aqueous phase. Gas exchange through the polymeric phase and into the aqueous phase solubilizes the carbon dioxide gas in the aqueous phase as carbonic acid which interacts with the buffer ions. The dye chosen is one which is responsive to the concentrations of the ionic species of the carbonic acid in the aqueous phase, i.e., an acid-base responsive dye.

For the purposes of this invention, we consider aqueous compositions which can be prepared by addition of various amounts of indicator, sodium bicarbonate, and a 50:50 mix of monobasic sodium phosphate and dibasic sodium phosphate. Those skilled in the art will recognize that these same compositions can be prepared in alternate ways without affecting the resultant buffer composition or the resultant buffer performance as a function of $CO_2$ partial pressure. Furthermore, it is recognized that the sodium ion or chloride ion as counterions for the buffering species can be replaced by other salt forming ions without changing the scope or intent of this invention.

Preferred for use in sensing carbon dioxide is a bicarbonate ion based buffer in the aqueous phase. Such a buffer can be chosen so as to have a buffer range compatible with the response range of the dye. Such a range might, for instance, mimic the physiological pH range of blood. Suitable for the preparation of such a bicarbonate ion buffer would be sodium bicarbonate, sodium carbonate and sodium hydroxide or other suitable buffer agents. For measuring blood carbon dioxide with hydroxypyrene trisulfonic acid, a pH range of pH 7.0 to pH 8.0 is the most desirable.

As discussed in Example 9, the concentration of the sodium bicarbonate and HPTS indicator can be chosen to optimize the sensitivity of the sensor over the range of $CO_2$ partial pressures commonly encountered during blood gas monitoring. In addition, this optimized sensitivity can be obtained at a higher sodium bicarbonate concentration by increasing the pKa of the indicator. This offers the advantage that for sensors containing only amine impurities, the amount of $CO_2$ conditioning drift can be reduced.

At high concentrations of sodium bicarbonate, the pH of the aqueous phase is high over the entire operating range of the sensor. When the operating pH range is sufficiently high relative to the pKa of the amine impurity, the impurity will be substantially deprotonated at all $CO_2$ partial pressures and will preferentially reside in the silicone phase. Sensitivity to amine induced drift scales inversely with sodium bicarbonate concentration over broad ranges of indicator concentration and phosphate buffer concentration.

The optimized sensor sensitivity can also be obtained at a low sodium bicarbonate concentration by using an indicator with a lower pKa. This offers the advantage that for sensors containing only acid impurities, the amount of $CO_2$ conditioning drift can be reduced. In this case, the acid induced $CO_2$ conditioning drift is minimized by working at buffer compositions prepared from low concentrations of sodium bicarbonate and higher concentrations of either the indicator, the phosphate buffer or both. The high concentration of indicator and/or phosphate buffer serves to buffer the aqueous phase against large pH changes when going from an air equilibrated state to 6% $CO_2$. In this case, an optimized sensitivity can still be achieved through proper choice of the carbonate, phosphate and indicator concentrations.

When there is a mixture of both acid and amine impurities in limited amounts, drift can be reduced by choosing an intermediate concentration of sodium bicarbonate to limit amine induced drift and a sufficiently high concentration of indicator and/or phosphate buffer to limit acid induced drift. In this case, an optimized sensitivity can still be achieved, but the change in pH on going from air to 6volume percent $CO_2$ is greatly reduced. Again, by increasing the concentration of the buffers and increasing the pKa of the indicator, optimum sensitivity can be maintained and amine induced drift can be reduced.

In choosing a dye for measuring carbon dioxide in blood, consideration is given to matching the pKa of the dye to the pH range of the aqueous phase induced by physical $CO_2$ levels. In constructing a gas sensor of this invention for use in sensing carbon dioxide gas in blood, we have found that hydroxypyrene 3,6,8-trisulfonic acid has characteristics which are superior to beta-methylum-belliferone, although beta-methylumbelliferone can also be used. Hydroxypyrene 3,6,8-trisulfonic acid, hereinafter referred to as HPTS, which is a known fluorescence dye for carbon dioxide, has a larger "Stokes shift" than does the umbelliferone compound. For use in fluorescence spectroscopy, this separates the excitation light from the emission light which improves the measurement of the emission light for improved gas sensor performance. The hydroxypyrene trisulfonic acid can be used as a free acid or as one of its salts as for instance an alkali or alkali earth salt.

Suitable indicator components for use in the present invention include: 9-amino-6-chloro-2-methoxyacridine; 2',7'-bis-(2-carboxyethyl)-5-(and-6)-carboxyfluorescein; 2',7'-bis-(2-carboxyethyl)-5-(and-6)-carboxyfluorescein, acetoxymethyl ester; 2',7'-bis-(2-carboxyethyl)-5-(and-6)-carboxyfluorescein, acetoxymethyl ester; 5-(and-6)-carboxy-2',7'-dichlorofluorescein; 5-(and -6)-carboxy-2',7'-dichlorofluorescein diacetate; 5-(and -6)-carboxy-4',5'-dimethylfluorescein; 5-(and-6)-carboxy-4',5'-dimethylfluorescein diacetate; 5-carboxyfluorescein; 6-carboxyfluorescein; 5-(and-6)-carboxyfluorescein; 5-carboxyfluorescein diacetate; 6-carboxyfluorescein diacetate; 5-carboxyfluorescein diacetate, acetoxymethyl ester; 5-(and -6)-carboxyfluorescein diacetate; 5-(and-6)-carboxynaphthofluorescein; 5-(and -6)-carboxynaphthofluorescein diacetate; 5-(and -6)-carboxySNAFL®-1, succinimidyl ester {5'(and 6')-succinimidylester-3,10-dihydroxy-spiro[7H-benzo[c]xanthene-7,1'(3'H)-isobenzofuran]-3'-one}; 5-(and 6)-carboxySNAFL®-2, succinimidyl ester {5'(and 6')-succinimidylester-9-chloro-3,10-dihydroxy-spiro[7H-benzo[c] xanthene-7,1'(3'H)-isobenzofuran]-3'-one}; carboxySNAFL®-1 {5'(and 6')-carboxy-3,10-dihydroxy-spiro[7H-benzo[c]xanthene-7,1'(3'H)-isobenzofuran]-3'-one}; carboxySNAFL®-1 diacetate {5'(and 6')-carboxy-3,10-diacetoxy-spiro[7H-benzo[c]xanthene-7,1'(3'H)-isobenzofuran]-3'-one}; carboxySNAFL®-2 {5'(and 6')-carboxy-9-chloro-3,10-dihydroxy-spiro[7H-benzo[c]xanthene-7, 1'(3'H)-isobenzofuran]-3'-one}; carboxySNAFL®-2 diacetate {5'(and 6')-carboxy-9-chloro-3,10-diacetoxy-spiro [7H-benzo[c]xanthene-7,1'(3'H)-isobenzofuran-3'-one}; carboxySNARF®-1{5'(and 6')-carboxy-10-dimethylamino-3-hydroxy-spiro[7H-benzo[c]xanthene-7,1'(3'H)-isobenzofuran]-3'-one}; carboxySNARF®-1, AM acetate {3-acetoxy-5'-acetoxymethoxycarbonyl-10-dimethylamino-spiro [7H-benzo[c]xanthene-7,1'(3'H)-isobenzofuran]-3'-one}; carboxySNARF®-2 {5'(and 6')-carboxy-10-diethylamino-3-hydroxy-spiro[7H-benzo[c]xanthene-7,1'(3'H)-isobenzofuran]-3'-one}; carboxySNARF®-2, AM acetate {3-acetoxy-5'-acetoxymethoxycarbonyl-10-diethylamine-3-hydroxy-spiro[7H-benzo[c]xanthene-7,1'(3'H)-isobenzofuran]-3'-one}; carboxySNARF®-6 {5'(and 6')-carboxy-10-diethylamino-3-hydroxy-spiro[7H-benzo[c] xanthene-7,1'(3'H)-isobenzofuran]-3'-one};
carboxySNARF®-X {5'(and 6')-carboxy-3-hydroxy-tetrahydroquinolizino[1,9-]-hi]spiro[7H-benzo[c]xanthene-7, 1'(3'H)-isobenzofuran]-3'-one}; 5-chloromethylfluorescein diacetate; 4-chloromethyl-7-hydroxycoumarin; Cl-NERF {4-[2-chloro-6-(ethylamino)-7-methyl-3-oxo-3H-xanthen-9-yl]-1,3-benzene-dicarboxylic acid}; dextran, BCECF, 00,000 MW, anionic {dextran, 2',7'-bis(2-carboxyethyl)-5(and 6)-carboxy-fluorescein, anionic}; dextran, BCECF, 40,000 MW, anionic; dextran, BCECF, 70,000 MW, anionic; dextran, Cl-NERF, 10,000 MW, anionic; dextran, Cl-NERF, 70,000 MW, anionic; dextran, Cl-NERF, 10,000 MW, anionic, lysine fixable; dextran, DM-NERF, 10,000 MW, anionic {dextran, 4-[2,7-dimethyl-6-(ethylamino)-3-oxo-3H-xanthen-9-yl]-1,3-benzene dicarboxylic acid, anionic}; dextran, DM-NERF, 70,000 MW, anionic; dextran, DM-NERF, 10,000 MW, anionic, lysine fixable; dextran, 7-hydroxycoumarin, 10,000 MW, neutral; dextran, 7-hydroxycoumarin, 70,000 MW, neutral; dextran, b-methylumbelliferone, 10,000 MW, neutral; dextran, b-methylumbelliferone, 70,000 MW, neutral; dextran, SNAFL®-2, 10,000 MW, anionic {dextran, 9-chloro-3,10-dihydroxy-spiro[7H-benzo[c]xanthene-7,1'(3'H)-isobenzofuran]3'-one, anionic}; dextran, SNAFL®-2, 70,000 MW, anionic {dextran, 10-dimethylamino-3-hydroxy-spiro[7H-benzo[c]xanthene-7,1'(3'H)-isobenzofuran]-3'-one, anionic}; dextran, SNARF®-1, 10,000 MW, anionic; dextran, SNARF®-1, 70,000 MW, anionic; 1,4-dihydroxyphthalonitrile; DM-NERF {4-[2,7-dimethyl-6-ethylamino)-3-oxo-3H-xanthen-9-yl]1,3-benzene dicarboxylic acid}; fluorescein diacetate; 8-hydroxypyrene-1,3,6-trisulfonic acid, trisodium salt; naphthofluorescein; naphthofluorescein diacetate; SNAFL®-1 {3,10-dihydroxyspiro[7H-benzo[c]xanthene-7, 1'(3'H)-isobenzofuran]-3'-one}; and SNAFL®-1, diacetate {3,10-diacetoxy-spiro[7H-benzo[c]xanthene-7,1'(3'H)-isobenzofuran]-3'-one}. from Molecular Probes, Inc. "SNARF" and "SNAFL" are registered trademarks of Molecular Probes, Inc. The structures of many of the aforementioned indicator compounds are listed in "Handbook of Fluorescent Probes and Research Chemicals", 5th Edition, pages 129 to 141 (1992) by Richard P. Haugland. Also absorption dyes such as chlorophenol red, bromo cresol purple, nitrophenol, bromo thymol blue, pinachorome and phenol red could be used.

Preferably, the concentration of the dye in the aqueous phase would be from about 1 millimolar to about 20 millimolar with about a 2 to 8 millimolar solution being typically used. Generally the concentration of the phosphate buffer in the aqueous phase would be from about 1 millimolar to about 50 millimolar with about a 10 millimolar solution typically being used. Generally the concentration of the bicarbonate buffer in the aqueous phase would be from about 5 millimolar to about 200 millimolar, with about a 20 millimolar formal concentration being used.

Other particular gasses of interest for the gas sensor of this invention include ammonia, $SO_2$, and $NO_2$. For sensing ammonia a pH sensitive dye would be solubilized in the aqueous phase. Gas exchange through the polymeric phase and into the aqueous phase solubilize the ammonia gas in the aqueous phase which interacts with the buffer ions. The dye chosen is one which is responsive to the concentrations of the ionic species of the ammonia in the aqueous phase, i.e., an acid-base responsive dye. Preferred for use in sensing ammonia is a ammonium chloride ion based buffer in the aqueous phase. Such a buffer can be chosen so as to have a buffer range compatible with the response range of the dye. Suitable indicators for use in measuring ammonium concentration include acridine orange, 1-hydroxypyrene-3,6,8-trisulphonate, and 1-naphthol-4-sulphonate.

Certain properties of the emulsion or suspension between the aqueous phase and the polymeric precursor can be enhanced by adding additional agents herein identified by the terminology "emulsification enhancement agents". These emulsification enhancement agents enhance certain manufacturing properties such as shelf life of the gas sensor intermediates by stabilizing the emulsion and retarding dehydration of the aqueous phase. In general, these emulsification enhancement agents are hydrophilic macro molecules. By retarding the dehydration of the aqueous phase and/or retarding break down of the emulsion or suspension of the aqueous phase and the polymeric precursor, it is not mandatory to immediately polymerize the aqueous phase-polymeric precursor emulsion or suspension into the emulsoid gas sensor of the invention. With the addition of the emulsification enhancement agents, the emulsion or suspension of the aqueous phase and polymeric precursor is stable and can be set aside for formation into the emulsoid gas sensor of the invention at a later time. This reduces the need to adhere to a tight manufacturing schedule and reduces or prevents the generation of manufacturing "scrap materials" which are economically wasteful. If used, the emulsification enhancement agent would be present at from about 5% to about 50% by weight per weight of the water of the aqueous phase. Typically about a 10–20% by weight of the emulsification enhancement agent is used. The emulsification enhancement agents may, for example, thicken or increase the viscosity of the aqueous phase or may alternatively create a thermodynamically stable emulsion by acting as a surfactant.

A material commonly used to thicken the aqueous phase, hydroxyethylcellulose ("HEC"), has been discovered to introduce a significant contributor to drift (i.e., a source of migrating species). This is believed to be a consequence of residual sodium acetate species present in the HEC thickener, as received from the manufacturer. We have discovered that the use of alternative thickeners which are substantially free of migratable acid or base impurities substantially eliminates this drift contribution. Suitable thickeners for use in the present invention are those thickeners which when present in a sufficient amount to provide the necessary or desired thickening to the aqueous phase are substantially free of partitioning species which can migrate from the aqueous phase to the hydrophobic second phase and which substantially affect the concentration dependent signal (i.e., contribute to $CO_2$ conditioning drift). For example, we have discovered that poly(ethylene oxide) at 300,000 molecular weight (available from Union Carbide under the trademark Polyox WSR-N750) provides excellent results and doesn't appreciably contribute to drift. Although the Polyox material is stated by the manufacturer to contain some residual ammonia, we found that this residual ammonia appears to have little or no impact on drift. It is believed that any residual ammonia in the Polyox material is either below the concentration necessary to cause drift, or not retained by the sensor after manufacture of the emulsoid.

Alternatively, we have discovered that purification of the aforementioned HEC thickener (e.g., by a dialysis process to remove the sodium acetate) will eliminate the contribution by the thickener to drift in sensors that use HEC to thicken the aqueous phase.

Other suitable thickeners or emulsifiers (referred to collectively as "emulsification enhancement agents") can be utilized, as long as the previously stated criteria are met. For example, the use of a water soluble polymer is envisioned. Suitable water soluble polymers include: water soluble polyethers such as the aforementioned poly(ethylene oxide), and poly(ethylene glycol); water soluble vinyl or acryl polymers including, for example, poly(acrylamide), poly-(dimethylacrylamide), poly(vinylalcohol), poly(vinylmethyl acetamide), poly(vinylpyrollidone), poly(styrene sulfonate), and poly(acrylamidomethylproponesulfonic acid), poly(hydroxyethylacrylate), poly(hydroxymethylacrylate), poly-(acrylic acid), and poly(vinyl methyl ether); water soluble polysaccharide polymers including, for example, dextran, xanthan gum, guar gum, alginic acid, and carageenen; water soluble cellulosic derivatives such as the aforementioned hydroxyethylcellulose, hydroxypropyl cellulose, carboxymethylcellulose, methylcellulose, hydroxypropyl(methylcellulose), and hydroxybutyl(methylcellulose); and other polymers such as poly(ethyloxazoline) and poly(ethyleneimine). Copolymers of any of the above or other polymers are also of possible use.

The suitability of any particular material should be tested relative to the amount and processing conditions desired to be used. Some materials, such as the aforementioned poly-(ethylene oxide), are suitable for use without further purification and are stable to a wide range of processing conditions. In contrast, cellulosic derivatives (as exemplified by hydroxyethylcellulose) may need purification to reduce any contaminants to acceptable levels. The cellulosic materials are believed to be stable to a variety of processing conditions. In further contrast, polysaccharides (as exemplified by dextran) may be suitable for use as received and without purification, but when exposed to typical conditions found in steam autoclave (>100° C.), which is a common method of sterilization, are believed to be susceptible to degradation releasing drift-inducing carboxylic acids. Thus, suitable materials should be evaluated for their purity (or the ease by which they may be purified) and/or their ability to withstand autoclave conditions. In some cases it may be advantageous to choose the higher molecular weight version of a given water soluble polymer, in that this generally provides the highest viscosification for the lowest amount of polymer, thus allowing the amount of polymer added (with therein-containing impurity) to be held to a minimum.

Notably, from the point of view of drift it is not necessarily required that the water soluble polymer itself be strictly neutral, that is, free of charges or ionizable groups, since any groups bonded to a water soluble polymer may be substantially incapable of partitioning into the hydrophobic matrix. However, from the point of view of sensor functioning, the contribution of any ionizable polymer substituent to the aqueous phase buffering capacity, or the contribution of such an ionizable substituent, or any associated counterion, to the ionic strength of the aqueous phase, may need to be taken into account.

It should be recognizable that emulsification enhancement agents such as surfactants may also be employed, subject to the above criteria. These might include, for example, non-ionic surfactants such as the Silwet family of polyethylene oxide/silicone surfactants sold by Union Carbide. Other surfactants are possible. Suitable surfactants include ionic surfactants as long as any effect of the ions, either on the surfactant chain or mobile counterions, does not cause or promote drift.

A hydrophobic second phase (e.g., a polymeric phase) is chosen as a carrier for the aqueous phase and to maintain the individual microcompartments of the first phase in their dispersed form. The second phase must be permeable to the gas of interest. It must also be permeable to the wavelength or wavelengths of light utilized in the measurement of the gas of interest. Further, since it is necessary to maintain the aqueous phase isolated from the carrier fluid of the gas of interest, the second phase should be substantially impermeable to liquid water. In order to isolate the indicator and/or any other ingredients in the aqueous phase, the hydrophobic phase should also be impermeable to ionic species. As for instance if the aqueous phase contains a buffer, it is important to maintain the ionic concentration of the buffer ions constant and not to dilute out or to increase the concentration of these desired buffer ions.

Because of their high gas permeability and ionized hydrogen irapermeability, silicone polymers are preferred for use as the hydrophobic secondary phase which separates the aqueous phase and the medium being analyzed. We have also discovered that certain hydrophobic secondary phase materials used in traditional $CO_2$ sensors contribute to drift. It is believed that the traditional materials contain (or emit during the curing process) partitioning species (such as acids or bases) which can migrate from the hydrophobic phase to the aqueous phase in response to a $CO_2$ induced pH change in the aqueous phase and thereby contribute to $CO_2$ conditioning drift. We have discovered that by carefully selecting appropriate materials for use as the hydrophobic phase or by treating standard traditional materials to remove or immobilize the partitioning species a drift free sensor can be constructed.

In general, the polymeric phase can be prepared via several polymerization reactions. Aside from the above described addition type polymerization, the polymeric phase can also be prepared via free radical polymerization reactions using silicones having ethylenically unsaturated groups, via condensation polymerization reactions using silanol terminated silicones cross-linked with alkoxyl silanes using catalysts such as tin derivatives, or via photo-initiated polymerization using ultraviolet or visible light catalysts. Notably, certain condensation cure silicones liberate acetic acid during the curing process. These materials are preferably avoided as the liberated acetic acid is believed to be an effective partitioning compound. Purification of such materials after curing may eliminate these partitioning species and enable this type of silicone to be utilized.

In one presently preferred embodiment the polymeric phase is prepared via a photoinitiated polymerization reaction and optionally followed with a thermal polymerization reaction. This may be done using either UV, near IR, or visible light. In one embodiment a free-radical initiator is utilized to crosslink an acrylate or methacrylate functional silicone polymer. Alternatively, and preferably, a radiation activated hydrosilation reaction is employed. For example, one may employ: ($\eta^4$-cyclooctadiene)diarylplatinum complexes (U.S. Pat. No. 4,530,879, Drahnak, which is herein incorporated by reference); ($\eta^5$-cyclopentadienyl)trialkylplatinum complexes (U.S. Pat. No. 4,510,094, Drahnak, which is herein incorporated by reference); or ($\eta^5$-cyclopentadienyl)tri(=94 949 -aliphatic)-platinum complexes and a sensitizer that is capable of absorbing visible light (U.S. Pat. No. 4,916,169, Boardman et at., which is herein incorporated by reference) with traditional siloxane polymers and crosslinkers.

The use of a photo-activated catalyst results in a decrease in scrap and waste compared to typical silicone catalyst formulations which often provide incompletely cured sensors. This is because traditional sensors often comprise silicone polymers which are cross-linked using a Karstedt catalyst. This type of catalyst is often of variable quality and is prone to becoming poisoned. As a result much effort is expended to prepare sensors which then fail to adequately cure. Photo-activated systems are also preferred for their greater flexibility in manufacturing. Traditional silicone systems require careful attention to working time and setting time constraints. Great care must be taken to fully form the sensor within the working time of the silicone material. Failure to finish forming the sensor within the allotted time results in scrap product. Photo-activated materials are more convenient, since the activation step can be delayed until the sensor is completely and fully formed. This virtually eliminates waste due to premature setting.

Suitable photoinitiators for use in the present invention should not undesirably contribute to $CO_2$ conditioning drift or undesirably interfere with the transmission of either the excitation light signal or the emission light signal through the sensor. Notably, we have not to date observed any measurable contribution to drift by either a typical platinum hydrosilylation catalyst or the aforementioned UV-activated versions of this catalyst.

For use in forming a carbon dioxide gas sensor, polydimethysiloxane is particularly preferred. We have discovered that a particularly useful commercial polydimethysiloxane provides sensors with substantially drift free response. It is used in conjunction with a cross-linking agent and a platinum catalyst such as a Karstedt catalyst.

Various typical hydrosilylation-cure polydimethylsiloxanes were discovered to contribute to drift. In contrast, one particular class of silicones (e.g., SYL OFF 7690 and 7691 from Dow Corning) exhibited substantially lower drift. This preferred class is believed to include materials made without an amine catalyst (in contrast to the traditional amine catalysis route which is used for most commercially available silicones including those silicones listed in Table 1a as: "C", "D", "E", and "F"). It is presently believed that the catalyst in SYL OFF 7690 and 7691 may contribute less to the drift than the amine species present in the other materials because it is either present at a lower concentration or because it is less able to reversibly partition in response to pH changes. Additionally, we found what the contribution by the silicone materials to drift can be somewhat reduced even for the usual amine-catalyzed base polymers by heating them at elevated temperature and high vacuum (150° C., 2 mm Hg) for a period of time. Other purification/extraction techniques might also be used. Likewise, acid catalyzed materials, including many crosslinker materials, can be made less prone to contribute to drift if heat treated or "stripped" prior to use in the sensor.

From about 1 gram to about 4 grams of the aqueous solution would be added to about 10 grams of the polymeric precursor. Typically about 2 grams of the aqueous phase per 10 grams of the polymeric precursor is used. The cross-linking agent would be added from about 2% to about 20% by weight of the polymeric precursor with approximately 5% by weight with respect to the weight of the polymeric precursor typically being used.

In addition to the previously mentioned emulsification enhancement agents, dispersing agents, such as fillers, can be added to the hydrophobic polymer phase if desired. Such agents serve to stabilize the initially formed dispersion prior to final crosslinking or cure. These dispersing agents, when added to the hydrophobic phase, may also serve to enhance the structural characteristics of the hydrophobic phase after crosslinking. That is to say, the filler may serve to improve the mechanical strength or integrity of the cured matrix. Suitable hydrophobic dispersing agents include fumed silica, precipitated silica or finely divided silica. Depending on the polymeric phase material, catalyst molecules or particles might also remain in the polymeric phase after completion of the polymerization, as for instance metallic catalyst particles.

The filler should also be selected such that the undesirable partitioning species are not inadvertently brought into the sensor composition. For example, the Tullanox 500 fumed silica used in the representative formulation is known to contain a significant level of a basic species (introduced with a hydrophobic surface treatment). However, we have found this species to induce only a small, possibly negligible, amount of drift. The residual base (believed to be ammonia) likely leaves the sensor during storage or during processing of the sensor. Nevertheless, as an extra precaution, one may preferably use filler which has been heated under vacuum (e.g., for 12 hours at 150° C. and at 2 mm Hg) or a deammoniated filler such as Cabot TS530. Also preferred are silica fillers which have been hydrophobically treated by processes which do not result in the presence of basic impurities (such as Cabot TS 610 or Cabot TS 720).

In an illustrative embodiment of the invention the dye is present in a quantity of about 0.01 grams per 2 mls. of said buffer solution, the dye in the buffer solution is added to the polymeric precursor in a quantity of about 2 mls. of the dye in the buffer solution to about 10 grams of the polymeric precursor. The cross-linking agent is added in a quantity of about 0.5 gram of the cross-linking agent per 10 grams of the polymeric precursor and the catalyst is present in trace amounts (200 ppm).

When the mixture of the aqueous phase and the polymeric precursor is emulsified, a suitable homogenizer such as a Virtis 23 homogenizer is used. The emulsification enhancement agent contributes to stability of the emulsion or suspension such that it has an increased shelf life. When it is desired to form the gas sensor of the invention, the cross-linker and/or catalyst is added (if they are not already present in the polymeric precursor) or the sensor is exposed to visible light or UV light if a photosensitive initiator is present. These are gently stirred into the emulsion and the resulting mixture then shaped and cured. A very simple gas sensor can be formed by simply depositing a drop of the mixture of the emulsion and the cross-linking agent onto the end of a fiber optic fiber and allowing it to cure into an emulsoid directly on the end of the fiber. Alternatively, the emulsion mixture or a sheet of sensor material formed from the emulsion as described in copending U.S. Pat. application "Sensing Elements and Methods for Making Same", Ser. No. 08/159,799 can be placed in a sensor holder or "cassette" to form a sensor.

Following emulsification, the aqueous phase is present in the polymeric precursor in micro-compartments which are generally smaller than 5 microns. Typically a production gas sensor of the invention will have micro compartments of the aqueous phase in the polymeric phase wherein the majority of the population of the compartments will be on the order of 2 microns. It is, of course, realized that the particles will actually be in a statistical range of particle sizes, some slightly larger than the above noted sizes, some slightly smaller, depending on the emulsification procedure and apparatus.

Seen in FIG. 1 is a drop 10 of the emulsion or suspension of the aqueous phase in the polymeric precursor. As is evident, the micro-compartments 12 are dispersed in a uniform manner through the drop 10 of the emulsion.

Figure 2A:
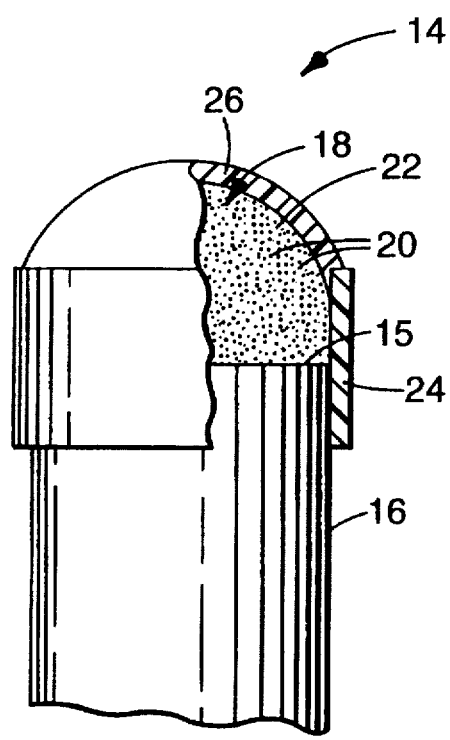
FIGS. 2a, 2b, 2c, and 2d are views in section of a gas sensor of the invention.
Figure 2A:

For formation of a very simple gas sensor 14 of this invention, in FIG. 2a, a drop of the above mixture is placed on the distal end 15 of an optical fiber 16. The mixture of the cross-linking agent and the polymeric precursor having the aqueous phase as an emulsion therein cures into an emulsoid 18 of the micro-compartments 20 of the aqueous phase in the polymeric material or cartier body 22. If desired, the emulsoid 18 can be retained on the end of the fiber 16 using a suitable sleeve 24. The sleeve 24 can be constructed from a suitable material such as Teflon or the like. Further, to avoid light intensity changes caused by factors other than the changes in partial pressure of the gas sensed, an overcoat 26 can be added as a layer over the exposed positions of the emulsoid 18. For use with a fluorescent dye, the overcoat 26 is chosen to be opaque to the excitation light wavelength $\lambda_{ex}$ and to the emission light wavelength $\lambda_{em}$ both of which are transmitted along the same single optical fiber 16. A suitable material for the overcoat 26 would be vinyl end-capped poly(dimethyl) siloxane impregnated with carbon black.

As is evident in FIG. 2a, the size of the gas sensor 14 is dictated only by the optical fiber size. The gas sensor 14 thus formed is of a sufficiently small size so as to be introducible directed into the cardiovascular system of a patient for direct real time measurement of the partial pressure of a blood gas such as carbon dioxide. If the fiber optic fiber 16 of FIG. 2a is typically about 125 micron in diameter, it is evident that the emulsoid 18 is approximately equal to or less than this size in each of its orthogonally oriented width, height and depth dimensions. Other constructions of gas sensors are also possible utilizing the emulsoid of this invention. It, of course, being realized that smaller sensors could be constructed by utilizing a smaller diameter fiber optic cable.

By using the above noted gas sensor construction in conjunction with HPTS as a pH sensitive dye, determination time of the carbon dioxide partial pressure is made in a time period of approximately one minute. This gas sensor can be autoclaved to sterilize it without detracting from or degrading its performance and during its use it is essentially temperature stable.

Figure 2B:
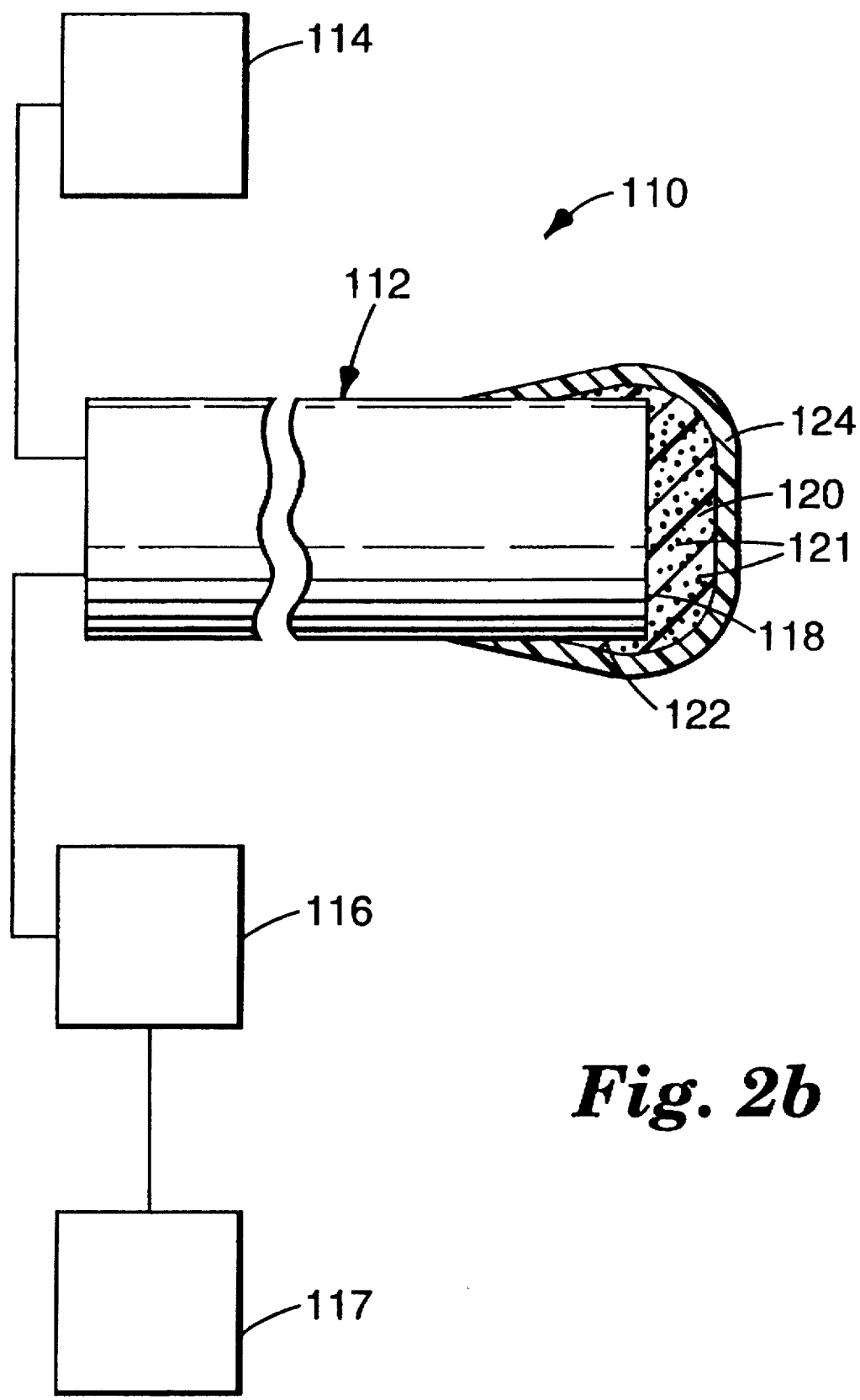

FIG. 2b shows a sensor 110 according to the present invention. Sensor 110 is adapted to determine the concentration or partial pressure of carbon dioxide in blood. An optical fiber 112 is connected to an appropriate light transmitting apparatus 114, which is capable of transmitting light at 410 and 460 nanometers. The light transmitting apparatus 114 generates the excitation light at these wavelengths. The optical fiber 112 is also connected to a light receiving apparatus 116, which, in turn, is connected to a conventional electronic processor 117. Located on the optical surface 118 of the optical fiber 112 is a matrix 120 which is a carbon dioxide permeable material, such as a cross-linked addition cured siloxane polymer. Within the matrix 120 is a plurality of micro-compartments 121 comprising an aqueous phase including HPTS indicator dye. The highly carbon dioxide permeable matrix 120 adheres to the optical surface 118 and slightly down along the sides 122 of the end of fiber 112. An opaque overcoating 124, comprising iron oxide pigment dispersed in an addition cured polysiloxane, can then be applied over the totality of the matrix 120 and down further along the side 122 of the fiber 112.

In use, sensor 110 functions as follows. The tip of optical fiber 112 including matrix 120 and overcoating 124 is exposed or immersed in blood, the carbon dioxide concentration of which is to be determined. Light transmitting apparatus 114 transmits light at 410 nanometers to the optical fiber 112. The excitation light at 410 nanometers causes the matrix 120 to fluoresce at 510 nm. In this case, the 410 nm light is absorbed primarily by the acidic form of HPTS. Excited state deprotonation follows, giving rise to 510 nm emission from the basic form of the dye. This emission is proportional to the amount of HPTS initially present in the acidic form. As the concentration of carbon dioxide in the blood increases, the pH of the aqueous phase drops and the intensity of 510 nm emission associated with 410 nm excitation increases. Light transmitting apparatus 114 then transmits light at 460 nm to the optical fiber. The excitation light at 460 nm also causes the matrix 120 to fluoresce at 510 nm. In this case, the 460 nm light is absorbed by the basic form of HPTS, which emits directly at 510 nm. This emission is proportional to the amount of dye initially present in the basic form. As the concentrate of carbon dioxide in the blood increases, the intensity of 510 nm emission associated with the 460 nm excitation decreases. The fluorescent emitted signals are transmitted from matrix 120 through optical fiber 112 to light receiving apparatus 116. Processor 117 uses information received by light receiving apparatus 116 on the longer emitted signal to determine a value of the carbon dioxide concentration in the blood. Receipt and analysis of this fluorescent light by light receiving apparatus 116 and processor 117 is carried out in a manner similar to that described in the above-referenced Lubbers, et al. U.S. Pat. No. RE 31,897 and in Heitzmann U.S. Pat. No. 4,557,900 each of which is incorporated in its entirety herein by reference. Processor 117 uses information received by light receiving apparatus 116 of the fluorescent signals emitted at 510 nanometers to develop a ratio of the emitted fluorescent signal associated with 460 nm excitation to the fluorescent signal associated with 410 nm excitation. Using this ratio together with the above-noted carbon dioxide concentration, processor 117 can determine a corrected concentration of carbon dioxide in the blood to be analyzed. This corrected carbon dioxide concentration is found to be accurate even if the optical fiber 112 is bent at one or more points along its length and/or if other light transmission difficulties are encountered.

The above-noted procedure may occur periodically or even substantially continuously to give substantially continuous carbon dioxide concentration results. Of course, the transmission of the excitation at 460 nanometers can take place before transmission of the excitation at 410 nanometers. Also, by proper selection of the optical indicators, e.g., fluorescent dyes, the concentration of other components of interest can be determined. In addition, media other than blood can be analyzed.

The optical fiber 112 may be in the form of a probe or a catheter insertable into a blood vessel of a patient to provide continuous on-line in vivo monitoring of oxygen concentration in the blood. Alternately, the present sensor can be embodied in a flow-through housing as shown, for example, in the above-referenced Heitzmann patent, to provide extra corporeal monitoring of carbon dioxide concentration in the blood. In this case it is often sufficient to monitor fluorescence associated only with the excitation at 460 or 410 nm.

Figure 2C:
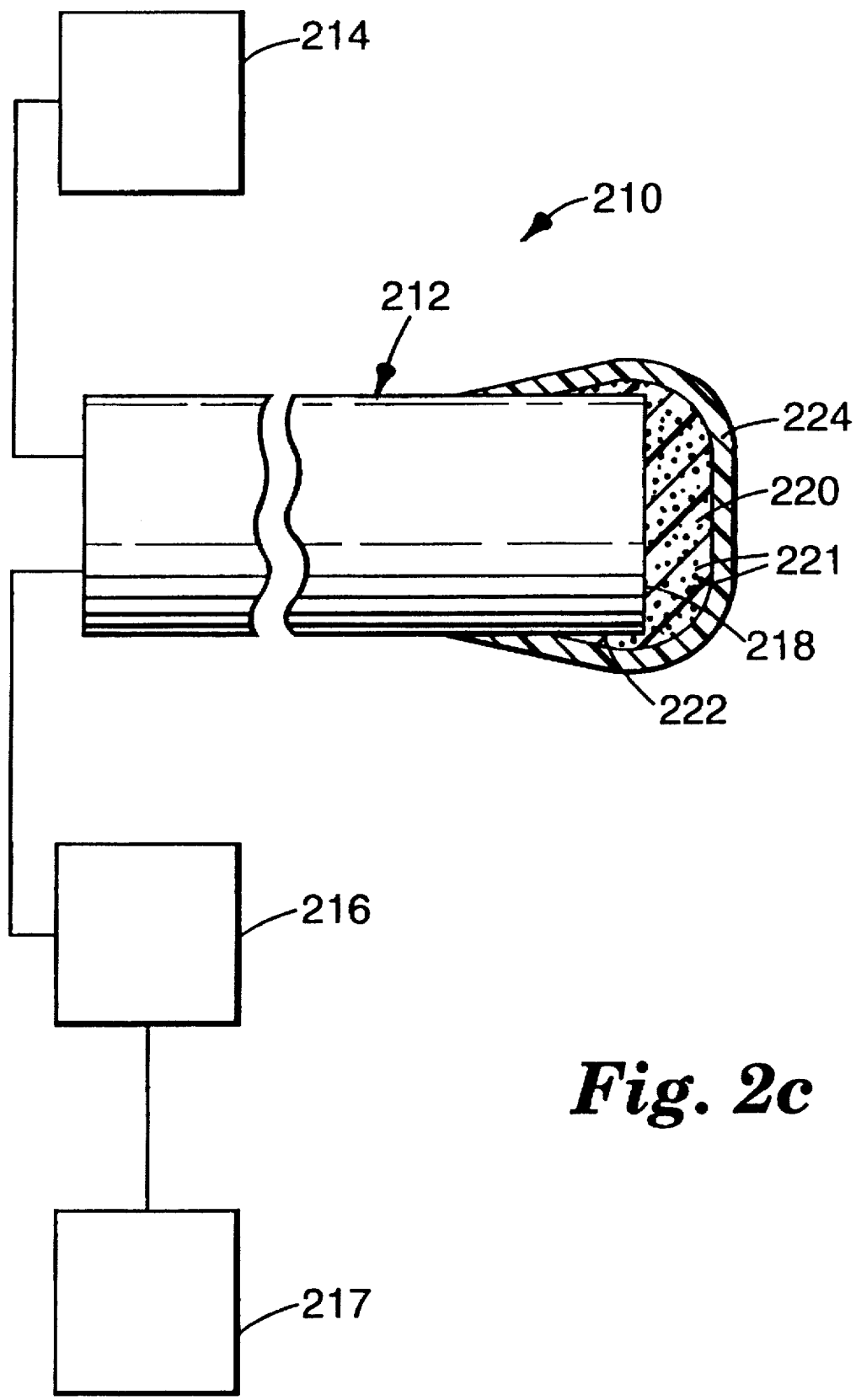

FIG. 2c shows a sensor 210 according to the present invention. Sensor 210 is adapted to determine the concentration or partial pressure of carbon dioxide in blood. An optical fiber 212 is connected to an appropriate light transmitting apparatus 2 14, which is capable of transmitting light at 543 nanometers. The light transmitting apparatus 214 generates the excitation light at this wavelength. The optical fiber 212 is also connected to a light receiving apparatus 216, which, in turn, is connected to a conventional electronic processor 217. Located on the optical surface 218 of the optical fiber 212 is a matrix 220 which is an carbon dioxide permeable material, such as a cross-linked addition cured siloxane polymer. Within the matrix 220 is a plurality of micro-compartments 221 comprising an aqueous phase including a dye (e.g., SNARF-6)-. The highly carbon dioxide permeable matrix 220 adheres to the optical surface 218 and slightly down along the sides 222 of the end of fiber 212. An opaque overcoating 224, comprising iron oxide pigment dispersed in an addition cured polysiloxane, can then be applied over the totality of the matrix 220 and down further along the side 222 of the fiber 212.

In use, sensor 210 functions as follows. The tip of optical fiber 212 including matrix 220 and overcoating 224 is exposed or immersed in blood, the carbon dioxide concentration of which is to be determined. Light transmitting apparatus 214 transmits light at 543 nanometers to the optical fiber 212. The excitation light at 543 nanometers causes the matrix 220 to fluoresce at two separate wavelengths. The emission at the shorter wavelength is associated with the acidic form of the indicator. The emission at the longer wavelength is associated with the basic form of the indicator. As the concentration of carbon dioxide in the blood increases, the pH of the aqueous compartment drops and the intensity of the short wavelength emission increases while the intensity of the long wavelength emission drops. Typically, the short wavelength emission is measured at 580 nm and the longer wavelength emission is measured at 630 nm. Both the emissions at 580 nanometers and 630 nanometers are dependent on the concentration of carbon dioxide in the blood. The fluorescent emitted signals are transmitted from matrix 220 through optical fiber 212 to light receiving apparatus 216. Processor 217 uses information received by light receiving apparatus 216 on the shorter emitted signal to determine a value of the carbon dioxide concentration in the blood. Receipt and analysis of this fluorescent light by light receiving apparatus 216 and processor 217 is carried out in a manner similar to that described in the above-referenced Lubbers, et at. U.S. Pat. No. RE 31,897 and in Heitzmann U.S. Pat. No. 4,557,900 each of which is incorporated in its entirety herein by reference. Processor 217 uses information received by light receiving apparatus 216 of the fluorescent signal emitted at 580 nanometers to develop a ratio of the emitted fluorescent signal at 580 nanometers to the fluorescent signal at 630 nanometers. Using this ratio together with the above-noted carbon dioxide concentration, processor 217 can determine a corrected concentration of carbon dioxide in the blood to be analyzed. This corrected carbon dioxide concentration is found to be accurate even if the optical fiber 212 is bent at one or more points along its length and/or if other light transmission difficulties are encountered.

The above-noted procedure may occur periodically or even substantially continuously to give substantially continuous carbon dioxide concentration results. Of course, the detection of the emission at 580 nanometers can take place before detection of the emission at 630 nanometers. Also, by proper selection of the optical indicators, e.g., fluorescent dyes, the concentration of other components of interest can be determined,, In addition, media other than blood can be analyzed.

The optical fiber 212 may be in the form of a probe or a catheter insertable into a blood vessel of a patient to provide continuous on-line in vivo monitoring of oxygen concentration in the blood. Alternately, the present sensor can be embodied in a flow-through housing as shown, for example, in the above-referenced Heitzmann patent, to provide extra corporeal monitoring of carbon dioxide concentration in the blood.

Figure 2D:
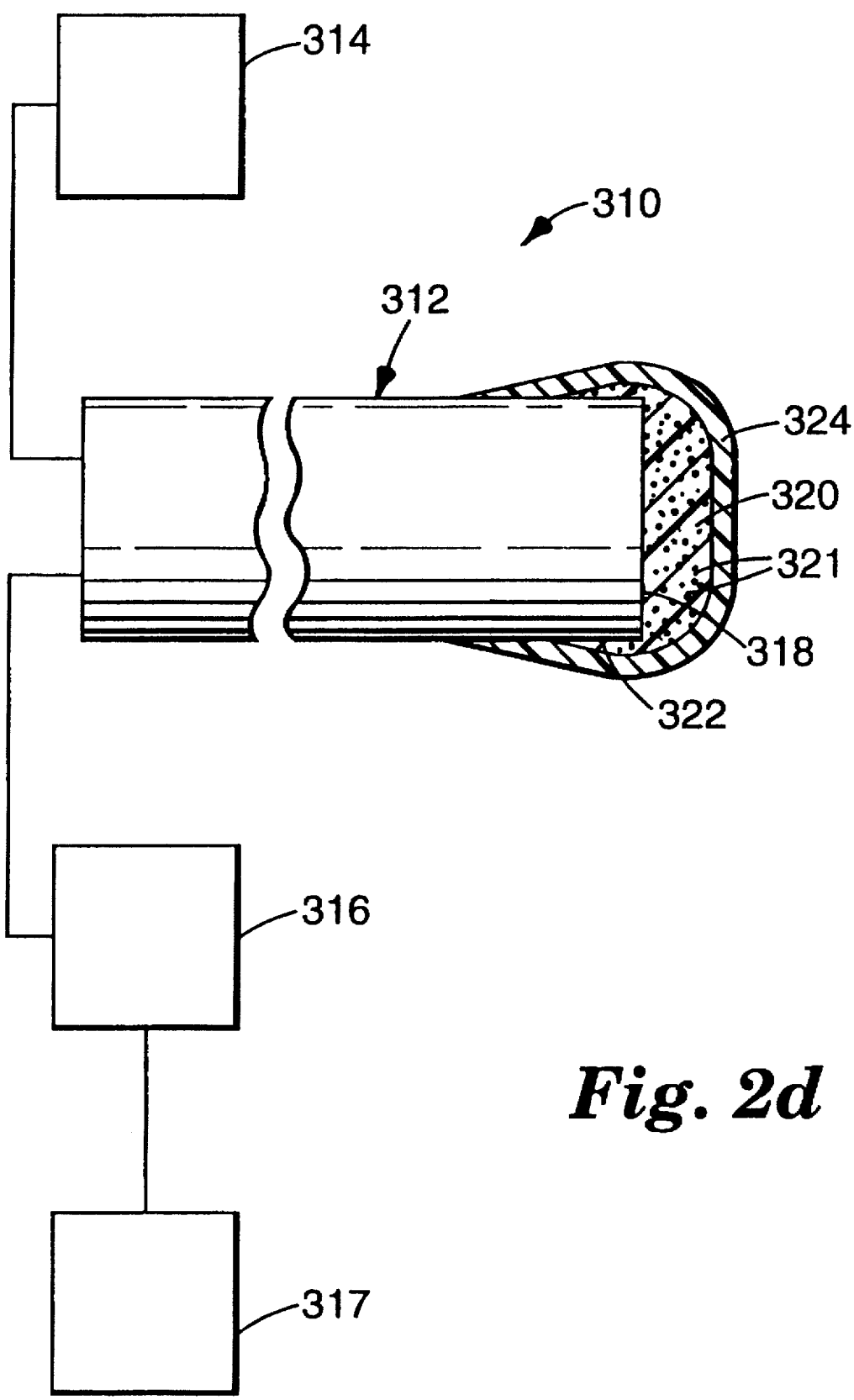

An alternate embodiment, which is described with reference to FIG. 2d, involves a sensor apparatus making use of intensity modulated (sine wave) signals in the MHz range. In this embodiment, sensor 310 is adapted to determine the concentration or partial pressure of carbon dioxide in blood. An optical fiber 312 is connected to an appropriate light transmitting apparatus 314, which is capable of transmitting intensity modulated (sine wave) light in the MHz range. The light transmitting apparatus 314 generates the modulated excitation light at this frequency. The optical fiber 312 is also connected to a light receiving apparatus 316, which, in turn, is connected to a conventional electronic processor 317. The light transmitting apparatus 314 includes a frequency generator (one or more frequencies simultaneously) linked to an electrically controlled light emitting structure, such as a light emitting diode, a frequency doubled light emitting diode, or a combination of elements such as a continuous wave laser or incandescent light source coupled to an acoustooptic modulator or electrooptic modulator, and the like. The light receiving apparatus 316 includes a highly sensitive light detector having a rapid response time. Suitable detectors include photomultiplier tubes such as those sold under the trademark R928 by Hamamatsu Photonics K. K., Hamamatsu, Japan, as well as avalanche photodiodes and microchannel plates, also available from the same supplier. Using techniques well known in the art, heterodyne detection can be implemented by modulating the detector sensitivity at a frequency, equal to the fundamental modulation frequency, $F_f$ in the MHz regime, plus or minus a heterodyne modulation frequency $F_h$ in the Hz or kHz region. The processor 317 may include, for example, an analog to digital converter coupled by a direct memory access device to a computer, or an analog phase comparator circuit known to those skilled in the art, and the like. The SLM 48000MHF Fourier Transform Spectrofluorometer manufactured by SLM-Aminco in conjunction with a HeNe laser provides frequency modulated light generation, light receiving apparatus and processor capability to perform the methods outlined herein; to measure phase shifts, demodulation factors, or both at either a single modulation frequency or simultaneously at several modulation frequencies. Commercial software is available to apply a well-known digital fast Fourier transform to the data and to interpret phase and demodulation data at multiple modulation frequencies in terms of a distribution of emission lifetimes and relative contributions.

Located on the optical surface 318 of the optical fiber 312 is a matrix 320 which is an carbon dioxide permeable material, such as a cross-linked addition cured siloxane polymer which is similar to the polymer described previously and containing a plurality of micro-compartments 321 comprising an aqueous phase comprising, for example, SNARF-6 dye (or any other suitable lifetime based pH indicator). The highly oxygen permeable matrix 320 adheres to the optical surface 318 and slightly down along the sides 322 of the end of fiber 312. An opaque overcoating 324, comprising iron oxide pigment dispersed in an addition cured polysiloxane, can then be applied over the totality of the matrix 320 and down further along the side 322 of the fiber 312.

In use, sensor 310 functions as follows. The tip of optical fiber 312 including matrix 320 and overcoating 324 is exposed or immersed in blood, the carbon dioxide concentration of which is to be determined. Light transmitting apparatus 314 transmits light at 50 MHz and 543 nm to the optical fiber 312. This excitation light causes the matrix 320 to fluoresce at 610 nm, an isobestic point for emission from the acid and base forms of SNARF-6. The fluorescent emission is sine wave modulated. The emission lifetime for the acidic form of the dye is longer than the emission lifetime of the basic form of the dye. As the concentration of carbon dioxide in the blood increases, the pH of the aqueous compartment drops and the phase shift increases while the demodulation factor decreases.

The fluorescent emitted signal is transmitted from matrix 320 through optical fiber 312 to light receiving apparatus 316. Processor 317 uses information received by light receiving apparatus 316 on the emitted signal to determine the extent of the phase shift and/or the demodulation factor of this emitted signal. The extent of this phase shift and/or this demodulation factor is dependent on the concentration of carbon dioxide in the blood. Thus, by determining the extent of this phase shift and/or this demodulation factor, values of the carbon dioxide concentration in the blood can be obtained. Transmission, receipt and analysis of this modulated signal by light transmitting apparatus 314, light receiving apparatus 316 and processor 317 may be carded out using equipment and in a manner similar to that described in Gratton U.S. Pat. No. 4,840,485 which is incorporated in its entirety herein by reference.

The above-noted procedure may occur periodically or even substantially continuously to give substantially continuous oxygen concentration results. Of course, by proper selection of the optical indicators, e.g., fluorescent dyes, the concentration of other components of interest can be determined. In addition, media other than blood can be analyzed.

The optical fiber 312 may be in the form of a probe or a catheter insertable into a blood vessel of a patient to provide continuous on-line in vivo monitoring of oxygen concentration in the blood. Alternately, the present sensor can be embodied in a flow-through housing as shown, for example, in the above-referenced Heitzmann patent, to provide extra corporeal monitoring of oxygen concentration in the blood. In addition, the light transmitting apparatus 314 and/or light receiving apparatus 316 may be embodied in the flow-through housing without an intermediate optical fiber.

Figure 5:
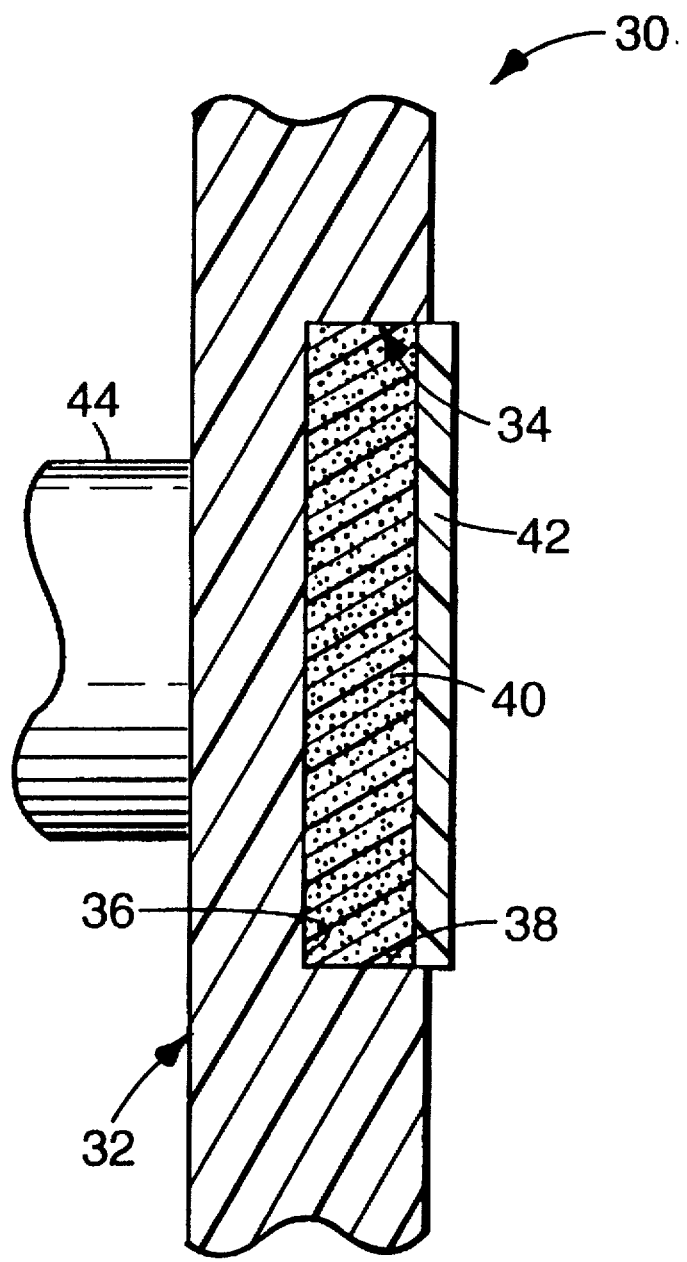
FIG. 5 is a view in section of a gas sensor of the present invention which comprises a flow through cassette comprising a sensing element.

Seen in FIG. 5 is a schematic representation of an alternative $CO_2$ sensor of the present invention. In this embodiment the gas sensor 30 comprises a "cassette" or sensor holder 32 having a well 34. The well 34 is open at one end, includes a bottom end wall 36 and a side wall 38. A drop of emulsion 10 is placed in the well 34 and cured to form an emulsoid 40. An opaque layer 42 can be added as a layer over the exposed positions of the emulsoid 40. In operation, a medium such as blood is brought in contact with the exposed portion of the emulsoid 40 (or alternatively in contact with the opaque layer 42). An excitation signal is transmitted through an optical fiber 44 which causes an emission signal from the indicator component. Alternatively, instead of using an optical fiber 44 to transmit the excitation and emission signals, one might either directly embed an LED and/or photodetector in the cassette or place an LED and/or photodetector in contact with the cassette (not shown).

The following examples are offered to aid in the understanding of the present invention and are not to be construed as limiting the scope thereof. Unless otherwise indicated, all parts and percentages are by weight except that $CO_2$ gas compositions are expressed by volume percent or in terms of partial pressure in mm Hg.

EXAMPLES

Example 1

An aqueous solution is prepared containing 6.36 mM hydroxypyrenetrisulfonate (trisodium salt), 6.6 mM sodium carbonate buffer, 71 mM sodium chloride and 10% by weight of poly(ethylene oxide) having a viscosity average molecular weight of 300,000.

0.5 gm of this solution is added to 2.0 gm of a vinyl terminated poly(dimethylsiloxane) sold by Dow Corning under the trademark SYL OFF 7690, to which is added 0.075 gm of fumed silica, sold by Cabot under the trademark TS-530. This fumed silica is deammoniated prior to being sold.

This mixture is homogenized three (3) times for 20 seconds each using a Tissue-Tearor high shear homogenizer, with the sample being briefly water cooled between each treatment. The resulting dispersion is degassed for one (1) minute under vacuum. 200 ppm Coy weight) of an ultraviolet light activated hydrosilylation catalyst component (cyclopentadienyl trimethyl platinum) is then added and 0.025 gm of a poly (dimethyl) (methylhydro) siloxane, sold by Dow Corning under the trademark SYL OFF-7678, is stirred in. This mixture has a silicon-bonded hydride/vinyl mole ratio of about 1.5. The mixture is again degassed. The degassed mixture is then cast into two (2) cavities of a sensor cassette made of polycarbonate. The cassette is then exposed to an ultraviolet sun lamp for 1.5 minutes on each side (approx. 15 mJ/cm$^2$) to activate the catalyst component thereby causing the mixture to crosslink or "cure". After this, the cassette is placed in an oven at 60° C. for 20 minutes to finish the curing of the mixture. The sensor cassette is then stored in the dark in normal saline until tested.

The amount of "$CO_2$ conditioning drift" a particular sensor exhibits is measured using the following standard protocol. First, the sensor is equilibrated in an air equilibrated medium at 37° C. using a recirculating aqueous loop sparged with air (i.e., having 0.25 mm $CO_2$) By "equilibrated" is meant that the sensor is exposed to the medium (e.g., using an air sparged aqueous loop) for a sufficient time period such that it becomes fully adjusted to the medium (i.e., the sensor is in a thermodynamic "rest" state where it no longer is "adjusting" to a new state, e.g., such as when partitioning species react to a new state and are in flux within a sensor). This air equilibrated rest state is designed to simulate the initial conditions a sensor exhibits when it is first manufactured or when the sensor is exposed to an air equilibrated medium such as a saline solution drip line. The sensor is then attached to a suitable excitation and detection assembly and a baseline measurement is obtained. The baseline measurement should be essentially constant and may, for example, be expressed in units of intensity or voltage which are then easily convened to p$CO_2$ (units of mm Hg) by comparison to a calibration curve.

After the sensor has come into a condition of equilibration with the air equilibrated medium a step change is made to a new $CO_2$ level by exposing the sensor to a medium which has been equilibrated with a gas having a p$CO_2$ of 45.6 mm (i.e., a gas having 6 volume percent $CO_2$). This new $CO_2$ level approximates a typical physiological level in a patient. This step change can be accomplished by quickly moving the sensor from the air equilibrated medium to a medium which is equilibrated with a gas having a p$CO_2$ Of 45.6 mm Hg. Alternatively, the medium surrounding the sensor can be quickly changed.

Figure 3A:
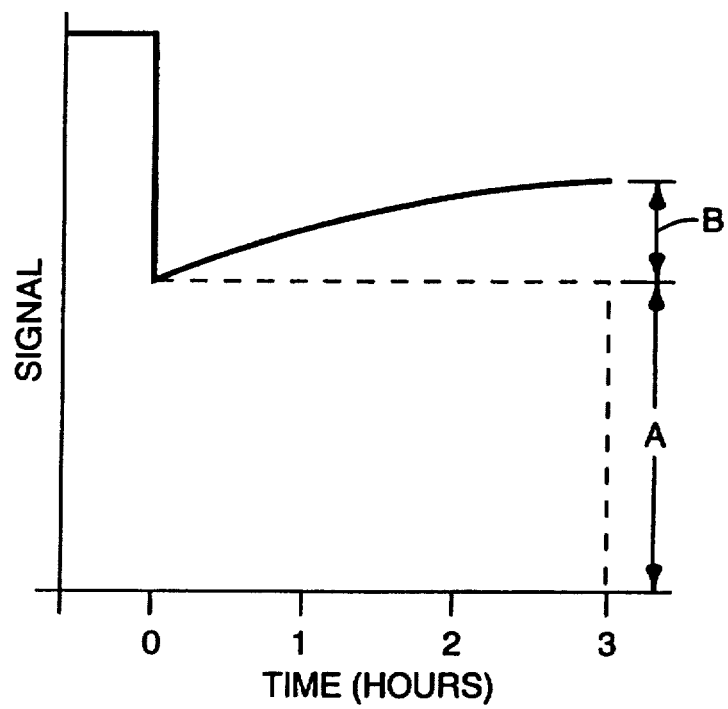
FIGS. 3a and 3b are plots illustrating $CO_2$ conditioning drift for a conventional sensor, the plots have been annotated to help describe two alternative methods of quantifying the drift.

Typically, after a rapid (less than about 5 minutes) initial signal response to the new $CO_2$ level, the sensor exhibits a slow $CO_2$ conditioning drift back towards the baseline signal level. This drift is most easily and reproducibly measured and reported as apparent "mm $CO_2$ drift" per hour over the course of a three hour exposure to the 45.6 mm $CO_2$ equilibrated medium. That is, the measured mm $CO_2$ at the end of the "physiological" exposure period (i.e., 3 hours at p$CO_2$=45.6 mm) minus the initial measured mm $CO_2$ just after the initial rapid response is divided by the number of hours of physiological exposure (i.e., 3). This is illustrated in FIG. 3$b$. The mm $CO_2$ drift per hour is equal to C/3. The percent mm drift per hour is equal to C/D·100/3. The drift may also be measured and reported as a percent of the change from the initial signal value of the sensor per hour over the course of a three hour exposure to the 6 volume percent $CO_2$ medium (although for purposes of this invention the method described in FIG. 3$b$ should be employed). That is, the signal reading at the end of the "physiological" exposure period (i.e., three hours at 6 vol. % $CO_2$) minus the "initial" signal reading just after the initial rapid response is divided by the initial signal reading, multiplied by 100, and then divided by the number of hours of physiological exposure (i.e., 3). This is illustrated in FIG. 3$a$. The percent drift is equal to B/A·100/3. The units of drift are the same units as used for the signal itself.

Note that for most sensors the drift is not linear over the three hour period. Thus, the slope of the drift line varies. For purposes of comparison, the mm $CO_2$ drift will (unless otherwise noted) be calculated as the average mm $CO_2$ drift per hour over the stated three hour period.

Also of importance for many diagnostic procedures is to minimize the total amount of $CO_2$ conditioning drift. As previously mentioned, the partitioning species react to a step change in pH. For sensors which are moved from a low $pCO_2$ medium to a higher $pCO_2$ medium this step change induces migration of various partitioning species. As a result of this migration a new equilibrium is reached. Eventually, the migration stops and the sensor is again stable (i.e., the signal has reached a plateau). The total mm $CO_2$ drift to reach this plateau is of particular importance for sensors which must remain in service for prolonged periods. One method of determining this plateau is to apply an exponential function to the 3 hour drift data and extrapolate the data to longer time periods (e.g., 24 hours). From this analysis one can approximate the total mm $CO_2$ drift.

For sensing gases other than $CO_2$, one may measure the analyte conditioning drift in an analogous manner. The drift is calculated by first conditioning the sensor in an analyte free medium, moving the sensor to a test medium containing the analyte, and measuring the drift away from the initial measured value. For comparison purposes, the test medium should have a concentration of analyte at the midpoint of the sensor's operating range.

Figure 3B:
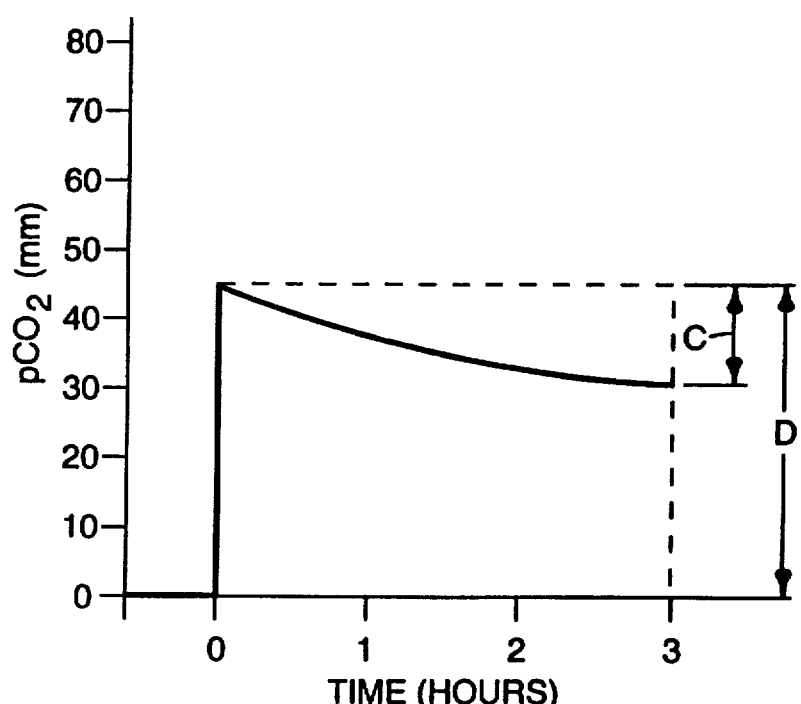

The sensing elements made in accordance with the above-described procedure (labeled as Run #1 in Table 1a) exhibit satisfactory sensitivity and time response, while typically exhibiting drift within the range of plus or minus 2.0% per hour (using the calculation method described in FIG. 3b). This level of drift is significantly lower than that of many typical representative formulations, e.g., Run 17, and approaches the clinical and/or practical limitations of the drift measuring apparatus and technique.

Run 1 was repeated using different materials, untreated or treated in different ways, as described in Table 1a. The selection or treatment of one or more of the components of the sensor is conducted to remove one or more of certain weakly acidic components and/or weakly basic components from the component or components. Each of the sensing elements produced was tested a number of times in accordance with the test procedure previously described (note that Runs #6 and 16 used an 8 volume percent $CO_2$ gas rather than a 6 volume percent $CO_2$ gas). Results of these tests are presented in Table 1a.

TABLE 1a

| | Silicone | | Crosslinker | | Silica | | |
|---|---|---|---|---|---|---|---|
| Run | Type[1] | Treatment[2] | Type[3] | Ratio[4] | Treatment[5] | Viscosifier[6] | Drift[7] (%/hr) |
| 1 | A | — | I | 1.5:1 | deamm. | PEO | <−2.0 |
| 2 | A | 150° C. | I | 1.5:1 | 150° C. | PEO | −0.94 |
| 3 | A | 150° C. | I | 1.5:1 | 150° C. | PEO | −0.52 |
| 4 | A | 150° C. | I | 1.5:1 | 150° C. | PEO | 0.81 |
| 5 | A | — | I | 1.5:1 | 150° C. | PEO | 0.32 |
| 6 | A | — | I | 1.5:1 | 150° C. | PEO | −0.30 |
| 7 | A | 150° C. | I | 10:1 | 150° C. | PEO | −2.87 |
| 8 | A | — | II | 2:1 | deamm. | PEO | −1.97 |
| 9 | A | — | II | 2:1 | deamm. | PEO | −0.78 |
| 10 | B | — | I | 1.5:1 | deamm. | PEO | −3.61 |
| 11 | C | 150° C. | I | 8:1 | 150° C. | PEO | −0.81 |
| 12 | C | 150° C. | III | 10:1 | 150° C. | PEO | −3.20 |
| 13 | C | 150° C. | III | 15:1 | 150° C. | PEO | −6.55 |
| 14 | C | — | III | 10:1 | 150° C. | PEO | −5.22 |
| 15 | C | 150° C | III | 10:1 | — | PEO | −3.84 |
| 16 | C | — | I | 8:1 | — | PEO | −3.36 |
| 17 | C | — | III | 8:1 | 150° C. | HEC | −16.5 |
| 18 | D | — | IV | 10:1 | 150° C. | HEC | −16.7 |
| 19 | E | — | V | 10:1 | 150° C. | HEC | −15.4 |
| 20 | F | — | VI | — | — | HEC | −15.4 |
| 21 | A | — | I | 1.5:1 | 150° C. | HEC | −8.92 |
| 22 | A | — | I | 1.5:1 | deamm. | HEC[8] | −1.40 |
| 23 | G | — | III | 8:1 | deamm. | PEO | −3.30 |

Footnotes for Table 1a:

[1]Silicone A is a vinyl functional poly(dimethylsiloxane) sold by Dow Corning under the trademark SYL OFF 7690.
Silicone B is a vinyl terminated poly(dimethylsiloxane) sold by Dow Corning under the trademark SYL OFF 7691.
Silicone C is a vinyl terminated poly(dimethylsiloxane) sold by Petrarch Systems under the trademark Petrarch PS 443.
Silicone D is a vinyl terminated poly(dimethylsiloxane) sold by Union Carbide under the trademark Y-7942.
Silicone E is a vinyl terminated poly(dimethylsiloxane) sold by NuSil Silicone Technology under the trademark NuSil PLY-7500.
Silicone F is a vinyl terminated poly(dimethylsiloxane) sold by Dow Corning under the trademark Q7-2218 part A.
Silicone G is a vinyl terminated poly(dimethylsiloxane) sold by Petrarch under the trademark PS-783.
[2]The heat treated samples were preprared using silicone polymer materials which were heated to 150° C. at 2 mm Hg for 12 hours.
[3]Crosslinker I is a poly(dimethyl) (methylhydro) siloxane sold by Dow Corning under the trademark SYL OFF 7678.
Crosslinker II is a silyhydride compound prepared as described in Example 1 of U.S. Pat. No. 4,822,687.
Crosslinker III is a poly(dimethyl) (methylhydro) siloxane sold by Petrarch Systems under the trademark PS 123.
Crosslinker IV is a poly(dimethyl) (methylhydro) siloxane sold by Union Carbide under the trademark Y 12247.
Crosslinker V is a poly(dimethyl) (methylhydro) siloxane sold by NuSil Silicone Technology under the trademark NuSil XL-123.
Crosslinker VI is a poly(dimethyl) (methylhydro) siloxane sold by Dow Corning under the trademark Q7-2218 part B.
[4]The ratio following the crosslinker designation refers to the mole ratio of silicon-bound hydride groups to vinyl groups in the precursor mixture. The crosslinker of Run #9 was further "stripped" by being fed at 10 ml/minute through a wiped-film evaporator maintained at 230° C.
[5]Each of the samples designated with a "—" or a "150° C." contained a fumed silica sold by Tulco under the trademark Tullanox 500. The heat treated samples were heated to 150° C. at 2 mm Hg for 12 hours. Each of the samples designated "deamm." contained a deammoniated fumed silica sold by Cabot under the trademark TS-530. This fumed silica is stated by the manufacturer to be a more completely deammoniated version of the Tullanox 500 fumed silica.
[6]Each of the samples contained a "viscosifier" in the aqueous phase. By "PEO" is meant poly(ethylene oxide) having a molecular weight of 300,000 and available from Union Carbide under the trademark WSR N-750. By "HEC" is meant hydroxyethylcellulose having a middle-viscosity and available from Fluka under the trademark "Hydroxyethylcellulose middle viscosity 1". Analysis of the HEC as received indicates that it contains sodium acetate and that a 10% solution of HEC in water would contain 3.3 mM sodium acetate.
[7]The drift value is an average drift value for at least two samples for each run and was calculated using the procedure described by FIG. 3b. Several of the runs were replicated more than twice.
[8]For this run the HEC was purified using the following process: To 20 gm HEC was added 400 ml deionized water. The solution was then dialyzed over a ten day period using Spectra-Pore 1 dialysis tubing (having a molecular weight cutoff of about 6,000 to 8,000 and a 1.46 cm diameter). The dialyzed material was then filtered through a 10 to 20 micron (μm) filter and freeze dried.

In general, sensors made with PEO viscosifier in the aqueous phase exhibited significantly less drift compared to sensors made with untreated HEC viscosifier. As previously mentioned, HEC is believed to contain residual amounts of sodium acetate which can serve as a partitioning species. Purification of the HEC material lessens drift considerably as illustrated by comparison of Runs #21 and 22.

In general, Silicones A and B advantageously exhibit lower contribution to drift than do Silicones C, D, and E. Silicones A and B are believed to be manufactured via a different technique than the amine catalysis route used in the manufacture of many commercially available silicones. Thus, the decreased contribution to drift might reflect a lower level of partitioning species (e.g., a silicone which is free of amines) as a result of the different catalysis process.

Alternatively, these silicones may contain partitioning species which are more easily removed during sensor construction and fabrication than the traditional silicone materials.

Somewhat better drift performance is obtained using Silicone A versus Silicone B. Since silicones A and B are believed to be made using the same general method of manufacture, the differences in drift observed when using the two polymers may possibly reflect differences in some structural characteristic of the polymer which affects the rate of partitioning of impurities into the cured polymer network.

In addition, the drift is somewhat reduced when using conventional aminecatalyzed silicone based polymers by heat treating the silicone at elevated temperature and high vacuum, as evidenced by comparison of Runs 12 and 14. Other purification techniques can also be employed to remove acidic and/or basic species from the components making up the sensing composition precursor.

As seen in Table 1a, it is evident that both the specific identity of the crosslinker and the ratio of hydride to vinyl can affect drift. For example, in general crosslinker I exhibits less contribution to drift than crosslinker III. This may reflect a difference in residual catalyst (typically acid catalysts are used in the synthesis of such crosslinkers). In addition, comparison of Run 4 to Run 7, and Run 12 to Run 13, reveal that lower hydride to vinyl ratios provides sensors with less drift. Finally, comparison of Run 8 to Run 9 indicates that further purification of a given crosslinker may serve to further reduce drift.

While the fumed silica used in a typical comparative formulation is known to contain a significant level of residual base resulting from a hydrophobic surface treatment, the present example demonstrates that this residual base induces only a small, possibly negligible, amount of drift (e.g, compare Run 12 to Run 15). The residual base is believed to be ammonia, which likely leaves the final sensor during storage. However, to lessen the possibility of contribution of this species to the drift, the fumed silica can be heated under high vacuum or a deammoniated fumed silica can be used.

Figure 4A:
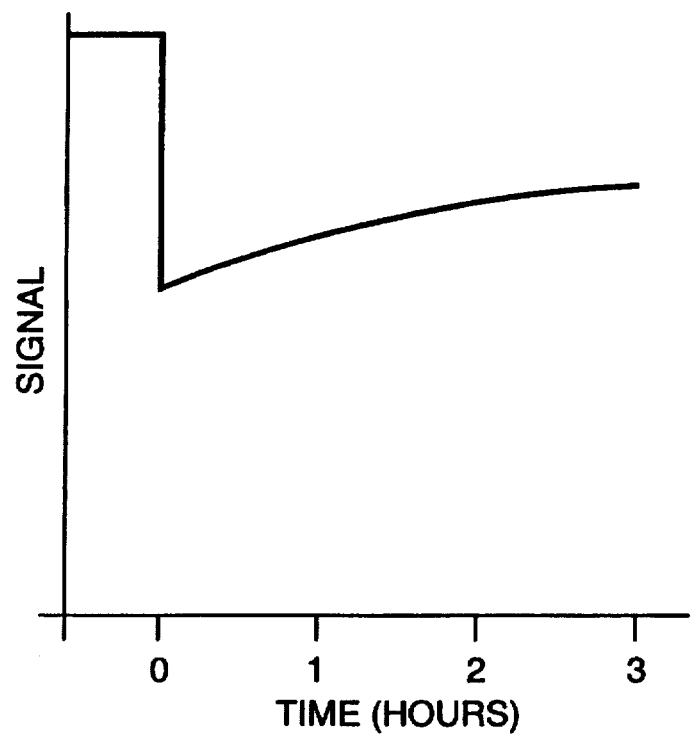
FIGS. 4a and 4b are comparison plots of two $CO_2$ sensors showing the improved drift stability of a sensor of the present invention compared to a conventional sensor.
Figure 4B:
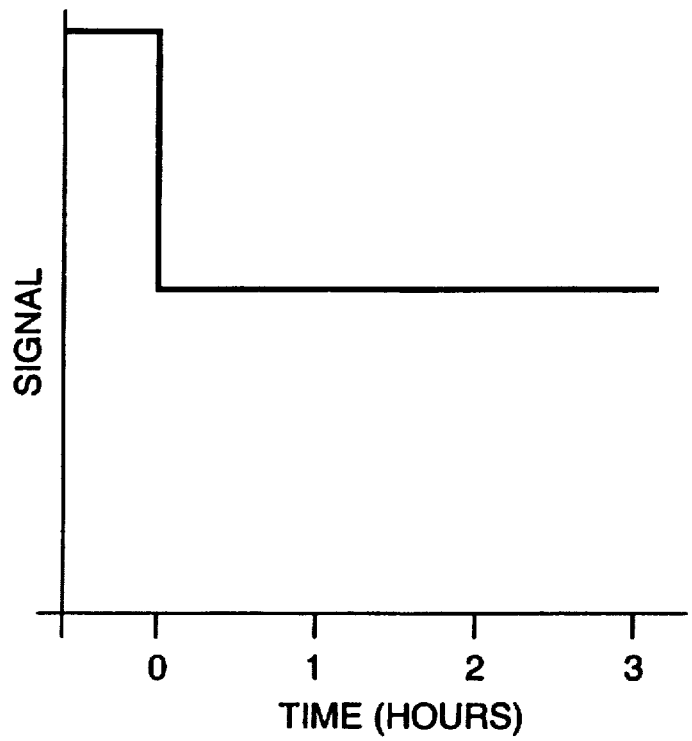

Referring to FIGS. 4a and 4b, a comparison of two runs of Example 1 are illustrated. FIG. 4a corresponds to one experimental measurement of the sensor of Run #20. The effect of $CO_2$ conditioning drift is evident and illustrates the problem encountered in traditional sensors. FIG. 4b corresponds to one experimental measurement of the sensor of Run #5. As illustrated by FIG. 4b, the sensor of Run #5 exhibits a stable signal with negligible drift over time.

Example 2

An aqueous solution is formed by dissolving 11.8 mg of hydroxypyrenetrisulfonate (trisodium salt), 375 mg of poly (ethylene oxide) having a molecular weight of 300,000 (sold by Union Carbide under the trademark WSR N-750), 31.4 mg of trisodium phosphate dodecahydrate, and 59.6 mg of sodium chloride in enough water to make 7.5 gm of solution.

A silicone mixture is prepared by combining 16.4 mg of cyclopentadienyl trimethyl platinum, (an ultraviolet light activated catalyst component), 0.49 gm of fumed silica, sold by Cabot under the trademark TS-530, and 15.91 gm of vinyl dimethyl end-capped poly(dimethyl siloxane) having a viscosity of 1000 centistokes sold by NuSil Silicone Technology under the trademark PLY 7500.

The aqueous solution is combined with the silicone mixture, and 1.1 gm of poly(dimethyl) (methylhydro) siloxane having a molecular weight of about 2100 and a silyl hydride group content of about 30%, sold by NuSil Silicone Technology under the trademark XL 123 is added. This combination is then processed with a Vertis Cyclone IQ homogenizer to form the sensing composition precursor.

A transparent polycarbonate web (available from Miles Inc. under the trademark DE 1-1), having a thickness of about 0.0127 cm, is coated with an adhesion enhancement component (available from Dow Corning under the trademark 1205 Prime Coat) derived from a mixture containing water, 1.25% by weight of colloidal silica particles, 0.11% by weight of aminopropyltriethoxysilane, 0.05% by weight ammonium hydroxide and 0.03% by weight of a surfactant sold by Rohm and Haas under the trademark Triton X-1000.

Using a coating apparatus sold by Hirano under the trademark M-200, the sensing composition precursor is continuously coated on one side of the web. In this coating operation (and all other coating operations described herein using this coating apparatus), the web is moved, at a constant speed, in proximity to and under the coating apparatus which is stationary. This precursor coating has a substantially uniform thickness of about 0.0025 cm. The sensing composition precursor is cured by exposing the coating to about 70 mJ cm$^{-2}$ Of ultraviolet (365 nm) light. The coating is further cured by exposure at about 90° C. for about 2 minutes to form the sensing composition.

An opaque film precursor is prepared by mixing 12 gm of a 12% by weight dispersion of carbon black, sold by Cabot under the trademark Regal 99R, in vinyl end-capped poly-(dimethyl)siloxane, having a viscosity of 500 centistokes (sold by NuSil Silicone Technology under the trademark PLY 7501), with 26.6 mg of a platinum catalyst solution sold by Nusil Silicone Technology under the trademark Cat50, 6.5 mg of a polymerization inhibitor sold by Nusil Silicone Technology under the trademark XL119, and 0.6 gm of the poly(dimethyl) (methylhydro) siloxane noted above. Using the coating apparatus noted above, this opaque precursor is continuously coated on the sensing layer in a substantially uniform coating with a thickness of about 0.0013 cm. The opaque film precursor is cured by exposure at 70° C. for 2 minutes to form the opaque film.

Figure 7:
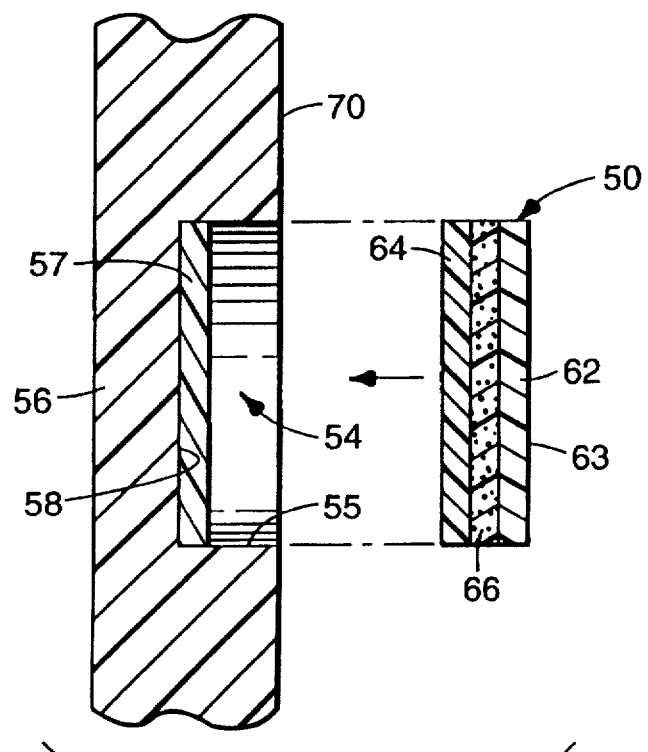
FIGS. 7 and 8 are two views in section of a gas sensor of the present invention which comprise a flow through cassette comprising a preformed laminate sheet sensing element.
Figure 8:
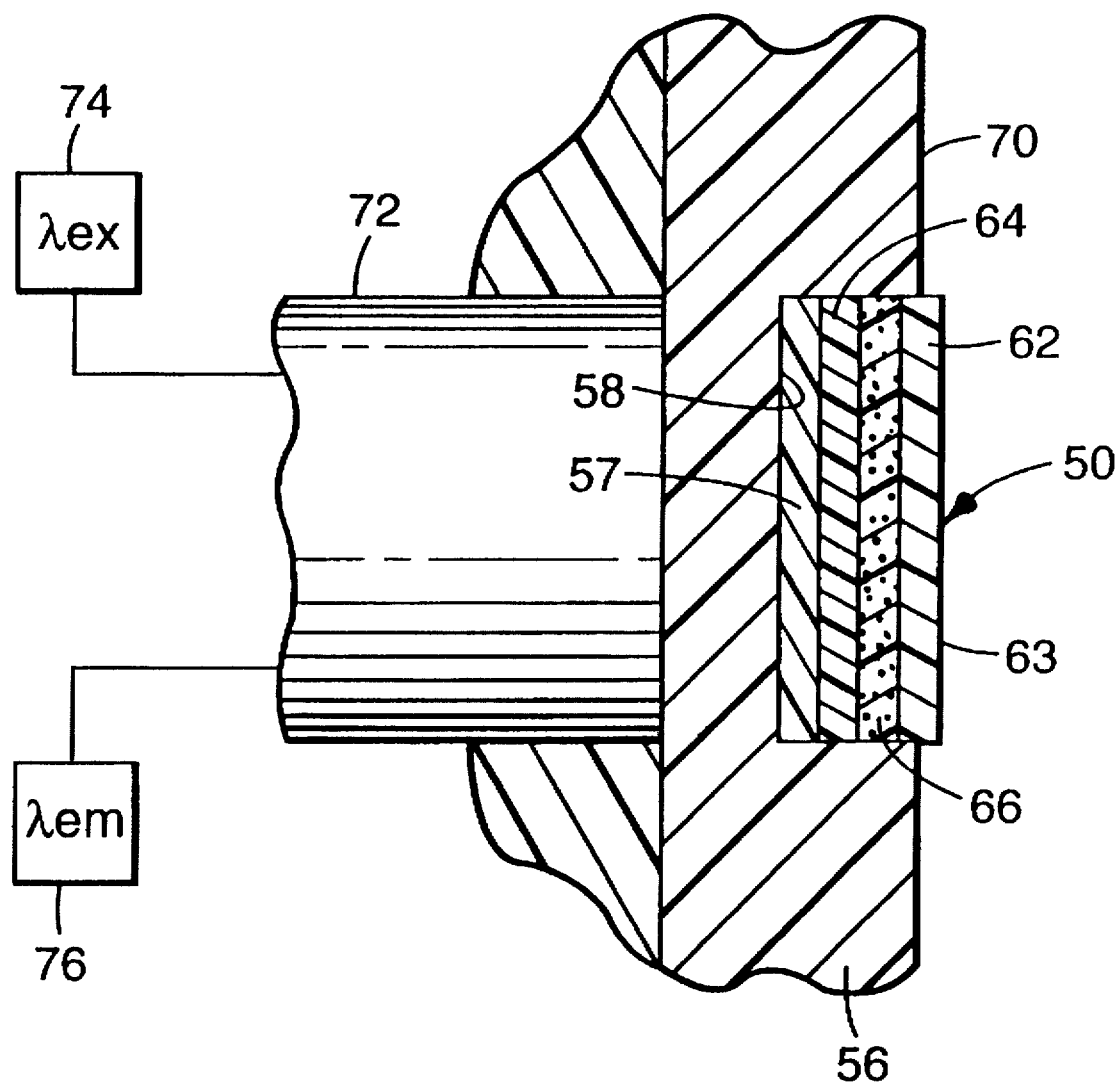

Individual carbon dioxide sensing elements are cut from the transparent web/sensing composition/opaque film composite. Each sensing element includes a generally circularly shaped portion of the transparent web, a generally circularly shaped portion of an opaque film and a thin, generally circularly shaped layer of the sensing composition therebetween. Such an individual sensing element is illustrated in FIGS. 7 and 8.

Using conventional testing procedures, a small, representative sample of the individual carbon dioxide sensing elements is tested to determine if such elements meet product specifications, that is if such elements are effective for accurately and reliably sensing the concentration of carbon dioxide in human blood. These individual carbon dioxide sensing elements are found to be satisfactory based on this testing procedure.

Using a transparent silicone-based adhesive sold by Dow Corning under the trademark 3140, one of these carbon dioxide sensing elements is bonded into a right circular cylindrical open ended well, having a diameter of 0.3175 cm and a depth of 0.025±0.0025 cm, formed in a polycarbonate cassette so that the transparent web layer is facing the bottom of the well. Prior to bonding the sensing elements to the cassette, the walls of the well are contacted with a priming agent, sold by Dow Corning under the trademark 1205, to promote adhesion between the sensing element and the polycarbonate cassette.

The thus produced carbon dioxide sensor is effective in determining the concentration of carbon dioxide in blood brought into contact with the opaque layer.

FIGS. 7 and 8 illustrate the use of a sensing element produced in Example 2 in determining carbon dioxide concentrations.

As shown in FIG. 7, this individual sensing element 50 is placed into well 54 containing a transparent, silicone-based adhesive 57. Well 54 is open at one end, includes a right circular cylindrical side wall 55 and a circular bottom end wall 58. The size of well 54 is such that the individual sensing element 50 and silicone-based adhesive layer 57 completely fill the well. Individual sensing element 50 is placed in well 54 so that the transparent web layer 64 faces the bottom end wall 58 of well 54. The opaque layer 62 includes an exposed surface 63 which is raised relative to the inner surface 70 of sensor holder 56. The opaque layer 62 substantially shields sensing composition layer 66 from direct contact with the medium, e.g., blood, to be monitored. Depending on the specific sensing application involved, the exposed surface of the opaque layer can be recessed relative to, or flush with, the inner surface of the sensor holder.

Referring now to FIG. 8, in use sensor holder 56, made of a transparent polycarbonate material, is placed in abutting relation to optical fiber 72. Optical fiber 72 provides excitation light of appropriate wavelength from light transmitting apparatus 74 to excite the sensing component in the sensing composition layer 66 to fluoresce and provide a signal characteristic of the concentration of carbon dioxide located in the medium in contact with the opaque film 62. This optical fiber 72 also transmits the signal which is emitted from the sensing component and passes such signal to a light receiving apparatus 76, which processes or analyzes this emitted signal, e.g., as described in Lubbers et al. U.S. Pat. No. Re 31,879, Heitzmann U.S. Pat. No. 4,557,900, and/or copending U.S. patent applications Ser. Nos. 08/136,967 and 08/137,289 to determine the concentration of carbon dioxide in this medium.

Over a period of time, the individual sensing element 50 provides consistent, e.g., substantially "drift" free, signals which are reliably correlated to the true and accurate concentration of carbon dioxide in the blood in contact with the opaque layer 62.

Example 3

Figure 6:
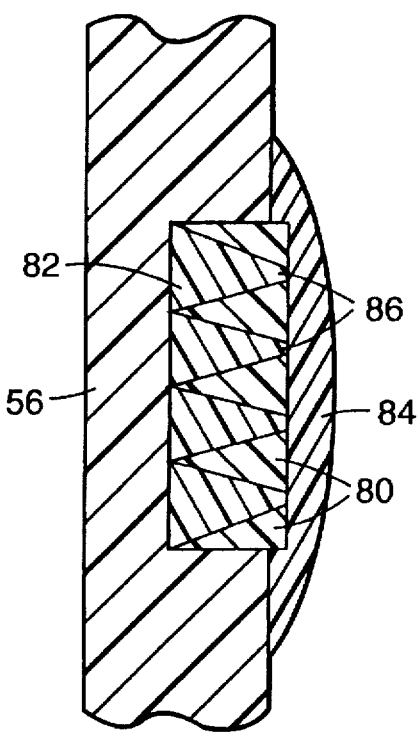
FIG. 6 is a view in section of a gas sensor of the present invention which comprises an asymmetric porous barrier film with an aqueous phase entrapped within the pores of the film.

Referring now to FIG. 6, an aqueous dye solution 82 was prepared as described in Example 1, Run #17. The dye solution was then sorbed into the pores of an asymmetric nylon membrane 80 made according to the method disclosed in Example 24 of U.S. Pat. No. 5,006,247, which is herein incorporated by reference. The dye solution/nylon membrane construction was then placed large pore side down into a sensor holder 56 having a right circular open ended well with a diameter of 0.4 cm and a depth of 0.013 cm. An overcoating of poly(dimethylsiloxane) 84 as described in Example 1, Run #17 was then applied and cured atop the upper surface of the nylon membrane (i.e., the surface having the small-pore openings 86). When tested according to the procedure described in Example 1 and FIG. 3b (but using an 8.0 volume percent $CO_2$ gas instead of the 6.0 volume percent CO: gas) this sensor exhibited less than −2% drift per hour, while maintaining excellent sensitivity and time response.

Nylon differs substantially from silicone in that small molecules (such as gases, organic vapors, and organic liquids) are much less soluble and much less diffusible in nylon than in silicone. Therefore the ability of species to partition from an aqueous phase into a nylon phase is greatly reduced compared to partitioning into a silicone phase. However, since the permeability of $CO_2$ through nylon is small, sensors using nylon as the hydrophobic phase or matrix would generally exhibit very slow response times. The asymmetric nylon membrane described herein possesses the unique advantage of having large structured pores which pass through the membrane and out one surface, but which have extremely small pore openings at the other surface. Thus, once the small pore opening surface is overcoated with silicone (achieving complete encapsulation of the aqueous phase), it is believed that the presence of the small nylon surface pores allow sufficient permeation of $CO_2$ through the silicone phase and into the encapsulated aqueous phase, but minimizes the interfacial area of contact between the encapsulated aqueous phase and the overlying silicone. This physical arrangement substantially reduces the rate of drift even in the presence of titratable impurities.

Example 4

A sensing composition was prepared as described in Example 1. Run #1 and formed into several individual sensing elements. Each individual sensing element (having a diameter of 0.4 cm and a thickness of 0.013 cm) was covered with a layer of an optical isolation barrier. The optical isolation barrier serves the function of reducing the detection of extraneous light signals (i.e., stray light from external sources). The optical barrier in one case consisted of a black teflon film available from Chemical Fabrics Corp. under the tradename DF 1100. This film contains, on one side, an adhesive-receptive surface which is believed to contain residual acidic species. The optical barrier in another case consisted of an identical film which had been washed with a 10 mM aqueous bicarbonate solution for 25 minutes. The sensor comprising the washed optical barrier exhibited drift of −5.5% per hour when tested as described in Example 1 and FIG. 3b. The sensor comprising the unwashed optical barrier film exhibited drift of about −16.3% per hour. A control sensor without an optical barrier film exhibited drift of about −0.15% per hour.

Example 5

Three sensing compositions were prepared as described in Example 1 and formed into several individual sensing elements. To each individual sensing element was added an optical isolation pigment as described below. A fourth sensing element without optical isolation pigment served as a control.

In a first case 0.2 wt. percent carbon black (Cabot Regal 99R) was added to the sensing element composition described in Example 1, Run #1. The composition was then formed, cured and tested as described in Example 1 and FIG. 3b. This sensor exhibited −2.2% drift per hour.

In a second case 2.0 wt. percent carbon black (Monarch 700) was added to the sensing element composition described in Example 1, Run #10. The composition was then formed, cured and tested as described in Example 1 and FIG. 3b. This sensor exhibited +1.3% drift per hour.

In a third case 9 wt. percent of a hydrophobically treated $TiO_2$ was added to the sensing element composition described in Example 1, Run #1. The $TiO_2$ material was treated with A-174 silane using an acetic acid catalyst. It is likely that some residual acetic acid species may remain after this treatment. The composition was then formed, cured and tested as described in Example 1 and FIG. 3b. This sensor exhibited −11.6% drift per hour.

In a fourth case a sensing element without isolation pigment was prepared as described in Example 1, Run #1. This sensor exhibited −1.2% drift per hour.

Example 6

A 25 gm solution of 100 mM sodium bicarbonate, 10 mM HPTS dye, was prepared. To this solution was added 5.0 gm of polyvinylpyrolidone ("PVP" having a 40,000 molecular weight and available from Aldrich Chemical Co.). The mixture was held at 37° C. for 14 hours to ensure solubilization of the PVP. The PVP-dye solution was then stored frozen until time of use.

0.46 gm of the above solution was added to 1.98 gm PS 783 silicone (available from Petrarch). A dispersion was formed by homogenizing the mixture using a Tissue-Tearor high shear homoginizer at the highest rpm setting. The mixture was homogenized three times (20 seconds each time).

To 0.51 gm of the above dispersion was added 5 microliters of photoactivatable hydrosilation catalyst solution and 0.046 gm PS 123 crosslinker (available from Petrarch). The catalyst and crosslinker were thoroughly stirred in for one minute with a glass capillary tube.

The above mixture was cast into two wells of a sensor holder. The sensor holder and mixture were then exposed to a UV sunlamp for 4 minutes (30 mJ/cm$^2$). This exposure caused the sensing elements to cure or crosslink to a nontacky condition. The sensors were then stored in an air-equilibrated aqueous saline medium until used.

In use the sensors were tested as follows. Two of the above cassettes were placed into a test loop and brought into an air-equilibrated state at 37° C. A step change was then introduced by moving the sensor to a 8.4 volume percent $CO_2$ medium (p$CO_2$=63.8 mm Hg). An initial fast intensity drop (within 4 minutes) was observed, followed by a gradual further downward drift in intensity over the course of the three hour exposure to the 8.4 volume percent $CO_2$ medium. The drift for four runs was calculated to be +13.9% per hour (41.7 percent over the three hour period of testing) when measured as described in FIG. 3b.

Examination of this formulation reveals that the components of the silicone phase, and the formulation procedure used, are typical of those components and procedures that are expected to contribute to $CO_2$ conditioning drift species. In particular, an amine-containing (i.e., amine catalyzed) silicone is employed in combination with a crosslinker which is demonstrated to contribute to drift. Furthermore, the hydride:vinyl ratio is high (8:1), which is demonstrated to further increase drift. The sensor of Example 1, Run #23 illustrates the use of the above silicone phase formulation in combination with a "clean" aqueous phase (i.e., a PEO-HPTS-carbonate solution which is demonstrated to not substantially contribute to drift). The resulting measured drift of Run #23 is due to the silicone phase materials.

Since the sensor of this example exhibits a positive mm drift, it is believed that the partitioning species of this sensor (perhaps due to the sensor's relatively high internal buffer concentration) may irreversibly migrate out of the sensor and into the medium (i.e., that "saline drift" predominates over "$CO_2$ conditioning drift").

As used herein, a sensor's "positive mm" drift or instability can be quantified by: (1) placing the sensor in a medium having a p$CO_2$ of 45.6 mm Hg and obtaining a first measurement of $CO_2$ partial pressure; (2) storing the sensor in a large capacity (i.e., a reservoir having sufficient capacity so as to act as a "sink" for any species migrating from the sensor) medium (having a p$CO_2$ of 0.25 mmHg and being free of any partitioning species) for a period of time (e.g., 24 hours); (3) placing the sensor in a medium having a p$CO_2$ of 45.6 mmHg and obtaining a second measurement of $CO_2$ partial pressure; and (4) comparing the first and second measurements (i.e., calculating the difference between the measurements).

Thus, a longer term drift, corresponding to the irreversible leaching of partitionable impurities out of the sensor chemistry, may be superimposed on the shorter term drift which corresponds to migration of partitionable impurities between the internal aqueous phase and the hydrophobic phase of the sensor.

Example 7

An alternative approach to producing $CO_2$ sensors involves attaching a pH sensitive dye to a hydrophilic polymer (e.g., bonding a pH sensitive dye to a functionalized hydrophilic polymer or copolymerizing a pH sensitive dye with a hydrophilic monomer). Frequently, acrylate or methacrylate monomers and/or polymers are employed. We have discovered that these acrylate based monomers and polymers typically contain residual quantities of acids (e.g., acrylic acid or methacrylic acid) inhibitors, and stabilizers. Unless measures are taken to remove these species the resulting sensor may be subject to drift.

The contribution to drift of the undesirable contaminants in a given substance can be evaluated by exposing a drift-free sensor to the contributing substance. In this example a low-drift $CO_2$ sensor (a film comprising an emulsoid as per Example 1, Run #1 and having a 0.4 cm diameter and a 0.013 cm thickness) was placed in a small container filled with an aqueous solution (1 ml capacity). On the inside surface of one side of the small container was placed 0.015 gm of the substance being investigated. The distance between the sample-spiked surface and the sensor is approximately 2.5 mm. The sensor was stored for five days and then tested as described in Example 1.

In a first run, no substance was coated on the inside surface of the container. The sensor had drift of 1.85 percent per hour when tested as per Example 1 and FIG. 3b. In a second run, 2(2-ethoxyethoxy)ethylacrylate (available from Sartomer Company under the tradename 256) was coated on the container. The sensor exhibited drift of 14.1 percent per hour. In a third run, tetrahydrofurfuralmethylacrylate (available from Sartomer Company under the tradename 203) was coated on the container. This substance had approximately 200 ppm acrylic acid and 30 ppm methacrylic acid. The sensor exhibited drift of 9.36 percent per hour. In a fourth run, tetrahydrofurfuralmethylacrylate (available from Scientific Polymer Products under the tradename M-130) was coated on the container. This substance had approximately 1.5 ppm acrylic acid. The sensor exhibited drift of 6.3 percent per hour. In a fifth run, tetrahydrofurfuralmethylacrylate (available from Scientific Polymer Products under the tradename M-130 and "purified" by Scientific Polymer Products to remove acidic species) was coated on the container. The sensor exhibited drift of 4.8 percent per hour.

These data illustrate that, if acrylate-based monomers are used in $CO_2$ sensor formulations (such as in the polymerization of hydrophilic monomers to form "hydrogels") precautions must be taken to remove drift contributing species from the monomer, or from the resulting polymer product.

Example 8

This example describes a $CO_2$ sensor configured for "on demand" monitoring. An aqueous mixture was prepared comprising 6.36 mM $Na_3HPTS$, 6.6 mM $Na_2CO_3$, 78 mM NaCl, and 10wt % hydroxyethylcellulose (available from Fluka). The mixture was held at 37° C. overnight to ensure complete mixing. To 0.5 gm of this dye mixture was added 2.0 gm PS 443 silicone base polymer (available from Petrarch) and 0.075 g of Tullinox 500 fumed silica filler. This mixture was homogenized and degassed for 3 minutes at 2 Torr. To prepare individual sensors, 0.5 g of the resulting dispersion was mixed with ten microliters of a thermally activated platinum catalyst solution (a 1 wt % solution of a Karstedt catalyst in toluene) and 0.25 gm of PS123 crosslinker (available from Petrarch). To prepare each sensor, a small amount of the resulting mixture was sandwiched between a black teflon membrane and a glass disk substrate (approximately 5 mm in diameter). The resulting sensors were placed in a 60° C. oven to crosslink. The black teflon membrane serves as an optical isolator and consisted of teflon impregnated with carbon black and a silicone adherent layer. The black teflon membranes were washed with sodium carbonate buffer before use. The completed sensors was then incorporated into a polycarbonate flow-through cassette by glueing the back of the glass disk substrate to the polycarbonate with a RTV silicone adhesive. Completed sensors were stored in a phosphate calibration buffer for several days before testing.

The sensors cassettes were tested in a saline drip line to mimic clinical monitoring of blood gases. Air equilibrated saline flowed through the sensor cassette at a rate of 1 ml/min between sample measurements. On-demand monitoring was accomplished by drawing a sample of $CO_2$ equilibrated phosphate buffer solution up the saline drip line and over the sensor. In clinical practice, blood would be drawn over the sensor from an arterial catheter. After five minutes, the phosphate buffer was flushed from the sensor cassette with fresh saline solution, and a slow air equilibrated saline drip was resumed.

The $CO_2$ sensor was excited at 460 nm, an excitation maximum for the deprotonated form of the HPTS indicator dye, and emission intensity was measured at 510 nm. During saline drip, the HPTS indicator is predominately in its basic form and the fluorescence intensity is high. At elevated $CO_2$ levels, the aqueous compartment pH drops and fluorescence intensity is reduced. The sensor was calibrated at two $CO_2$ concentrations and at 37° C. using phosphate calibration buffers sparged with either 2.8 or 8.4 volume % $CO_2$. A calibration relationship was determined.

Figure 9:
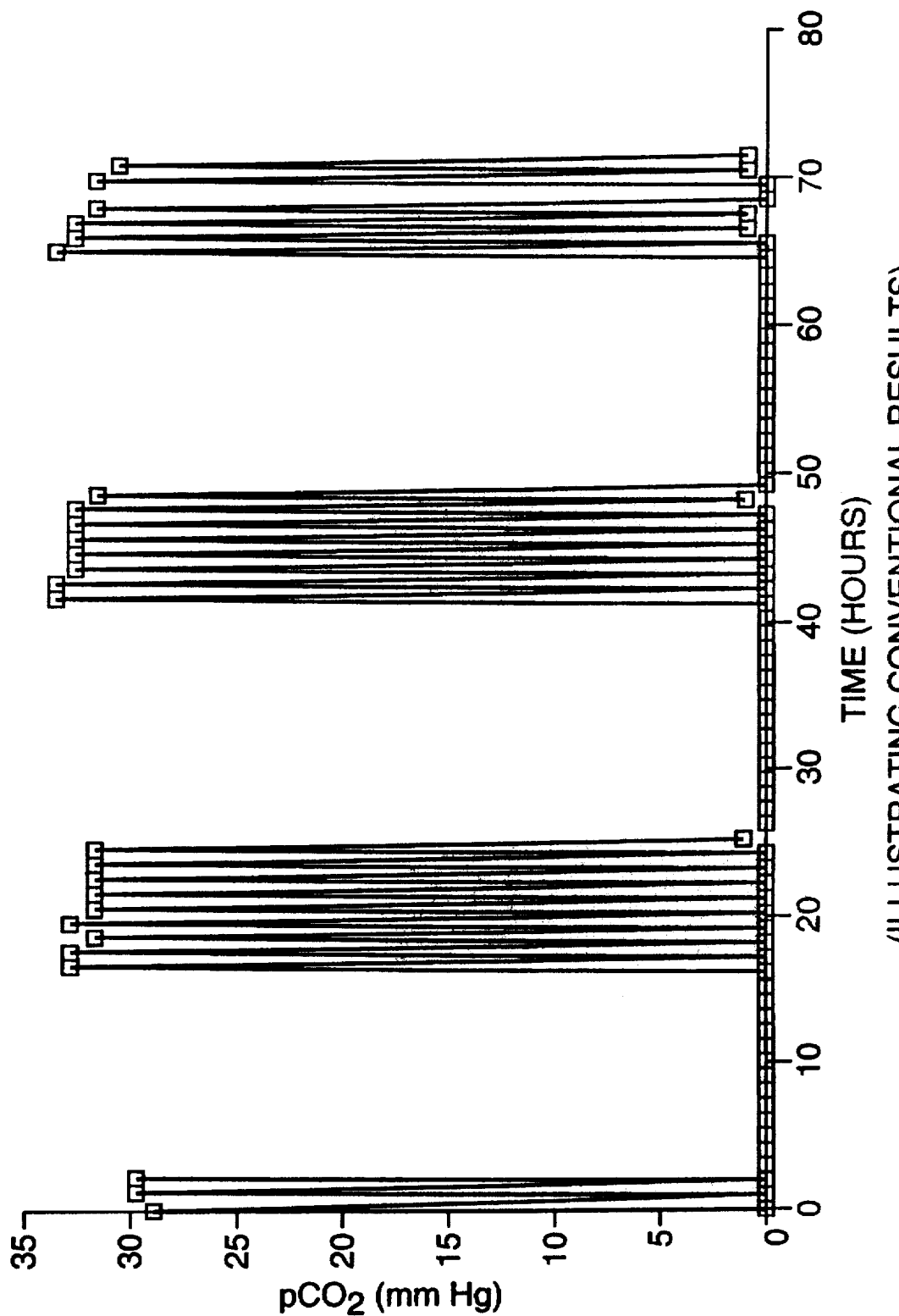
FIG. 9 is a graphical representation of $CO_2$ and saline drift for a conventional sensor.

FIG. 9 shows a typical response of a calibrated sensor. During the daytime, an "on demand" measurement of 5 volume % $CO_2$ sparged phosphate buffer was made once every hour. Between readings and at night, the sensor was exposed to an air equilibrated saline drip. During the second third and fourth days, when hourly measurements were made, there was a negative mm drift between successive readings. This drift was reversed during overnight saline drip. On the first day, the readings were low because the negative mm drift had already occurred during the sensor calibration process.

Careful inspection of the fluorescent intensities between samples indicated that a residual concentration of $CO_2$ in the sensor between sample draws. This residual $CO_2$ partial pressure was estimated to be about 0.5 mm Hg and went away after the first three hours of overnight saline drip. This was due to some reservoiring of residual $CO_2$ in the tubing and sensor cassette.

Using a species predominance model (described below in Example 10) to determine the thermodynamic state of the internal aqueous compartment as a function of $CO_2$ partial pressure, we calculated that the aqueous phase pH was always below 8.3 during the daytime (even between measurement periods), anti above 9.3 at night, while the osmolarity did not change appreciably during this period. This led us to conclude that the negative mm drift was the result of pH dependent migration of acid and/or amine impurities in and out of the internal aqueous phase. Furthermore, these species were present within the sensor and were not introduced from the medium being sensed. The negative mm drift was associated with the reversible migration of acid and amine impurities between the aqueous phase and the silicone phase.

There are several methods by which one may reduce this drift. First, one may effectively limit the amount of drift by reducing the driving force which causes the drift (i.e., the pH change in the internal aqueous compartment). This was accomplished by repeated sampling of the sensor in the 5 volume % $CO_2$ sparged phosphate buffer. In such a case, the residual $pCO_2$ was never below 0.5 mm Hg and thus the sensor is always below pH 8.3. The sensor pH was only changed by one unit when later exposed to the 5 volume % equilibrated medium (rather than by 2 units as would be the case for a sensor which starts at a $pCO_2$ of 0.25 mm Hg). Thus the amount of partitioning was reduced by a factor of 10. A similar result followed, if after exposure to the 5 volume percent medium the sensor was stored in medium having a $pCO_2$ of 0.5 mm Hg.

Drift free performance can also be achieved by employing a mixed carbonate/phosphate buffer in the internal aqueous compartment to keep the aqueous phase pH below 8.3 during the overnight saline drip period.

Notably, the black teflon overcoat can trap the migratable species in the sensor, making it more difficult to remove these migratable impurities by washing.

Example 9

We discovered that the two principle partitioning species in the sensors of Example 8 were acid (e.g., sodium acetate present from the manufacture of the hydroxyethylcellulose and other acids from the crosslinker) and base (e.g., ammonia from the manufacture of the silicone base polymer and the fumed silica filler) impurities. We have developed a species predominance model to determine the thermodynamic state of the internal aqueous compartment as a function of $CO_2$ partial pressure, buffer concentration, and the level of migratable impurities. Using this model as a guide, we can modify the buffer composition of the aqueous phase to minimize acid induced drift, amine induced drift, or both. By deconvolving acid and amine induced drift in this way, we are able to track down the source of impurities and arrive at a cleaner sensor composition. Also, we can formulate sensors with alternate buffer compositions and indicators that are more stable to drift in the presence of modest levels of impurities.

Model for the Aqueous Phase

The internal aqueous compartment is comprised of a mixture of buffers and additional salts. In the simplest case, there are the acid and base forms of the indicator dye, the various forms of carbonate buffer in equilibrium with a partial pressure of $CO_2$, and sodium chloride added to provide a desired osmolarity. The following representative equilibria apply.

$CO_2$ (gas) $\leftrightarrows$ $CO_2$ (dissolved)

$CO_2$ (dissolved) $\leftrightarrows$ $HCO_3^- + H^+$ $HCO_3^- \leftrightarrows CO_3^{2-} + H^+$ $HPTS^{3-}$(acid) $\leftrightarrows HPTS^{4-}$ (base)$+H^+$ When impurities are present (acetic acid and ammonia shown), the following representative equilibria additionally apply.

$CH_3OOH \leftrightarrows CH_3OO^- + H^+$ $NH_4^+ \leftrightarrows NH_3+$

Acid dissociation constants relate the concentration of each buffer species to the total buffer concentration and to the concentration of hydronium ions, as shown below for $CO_2$.

$$K_{CO2}' = \frac{[HCO_3^-][H^+]}{s\ pCO_2}$$

$$K_{HCO3-}' = \frac{[CO_3^{2-}][H^+]}{[HCO_3^-]}$$

where:

"s" is the molar concentration of dissolved $CO_2$ per unit partial pressure of $CO_2$ and as corrected for temperature and ionic strength effects according to experimental data.

We used experimental data in a lookup table to correct the $CO_2$ solubility "s" for temperature and ionic strength effects. We also corrected the acid dissociation constants for temperature and ionic strength effects using methods discussed later.

Our model iteratively converges on a self-consistent solution to the general equation for charge balance (equation 1), at a particular $CO_2$ partial pressure and at a fixed temperature.

$$[Na^+]+[H^+]-[OH^-]-[Cl^-]+\Sigma z_i C_i(H^+)=0 \quad \text{eq. 1}$$

where:

$z_i$ is the ionic charge of species i, and $C_i(H^+)$ is the pH dependent concentration of ionic buffer species. The ionic strength (I) is initially estimated from the concentration of excess sodium chloride concentration. From this, the $CO_2$ solubility and acid dissociation constants are estimated. These are used to estimate the concentrations of the acid and base forms of the buffers as a function of $H^+$ concentration. The $H^+$ concentration is then varied until equation 1 is satisfied. The preliminary solution for $[H^+]$ corresponds to a preliminary concentration of each buffer species. With this information, a new estimate of the ionic strength is made. In turn, the $CO_2$ solubility and acid dissociation constants are updated. The process is repeated until a self consistent solution for $[H^+]$ and I are obtained. This iterative process is repeated at each new partial pressure of $CO_2$ to determine sensor response characteristics.

Acid dissociation constants, $K_a$, are determined as follows. First, the acid dissociation constants are estimated at zero ionic strength and absolute temperature T using experimental data, summarized in functional form in equation 2.

$$-\log(K_a) = A_1/T - A_2 + A_3 T \quad \text{eq. 2}$$

Next, the ionic strength effects are determined. Traditional estimates of apparent acid dissociation constants ($K_a'$) require assumptions about the activity coefficients of individual ions, which cannot be measured experimentally. By assuming an excess of sodium chloride, we have recast the problem in terms of experimentally measurable parameters, namely the activity coefficients of ion pairs, f±. Sodium ion is the dominate counterion for negatively charged acids and bases; chloride ion is the dominant counterion for positively charged acids and bases. For charge neutral and anionic acids, the result is shown in equation 3, where J is the charge on the deprotonated form of the buffer. For cationic acids, the result is shown in equation 4.

$$K_a' = \frac{K_a(f_\pm \text{acid})^J (f_\pm \text{NaCl})^2}{(f_\pm \text{base})^{J+1}(f_\pm \text{HCl})^2} \quad \text{eq. 3}$$

$$K_a' = \frac{K_a(f_\pm \text{acid})^{J+2}}{(f_\pm \text{base})^{J+1}(f_\pm \text{HCl})^2} \quad \text{eq. 4}$$

Instead of using a lookup table, the ionic strength and temperature dependence of the experimental activity coefficients for each buffer species have been fit to the Debye-Huckel-Onsanger equation 5, where "a" and "b" are adjustable parameter related to ionic radius and specific ionic interactions, respectively, $z_1$ and $z_2$ are the ionic charges. A and B are thermodynamic parameters which depend on temperature and dielectric constant of the medium.

$$\log f_\pm = \frac{A|z_1 z_2| I^{1/2}}{1 + Ba I^{1/2}} + bI \quad \text{eq. 5}$$

To achieve a convergent solution to equation 1, each updated estimate of ionic strength is plugged into a family of equations of the form of equation 5 to determine activity coefficients for each ion pair. These activities are plugged into a family of equations of the form of equations 3 or 4 to update the estimates of the apparent acid dissociation constants for each buffer.

To estimate the sensitivity of a sensor to changes in $CO_2$ we calculate the pH of the aqueous phase at several $CO_2$ partial pressures. The concentration of the basic form of HPTS is calculated and fit to a mathematical relationship or calibration equation. Alternatively, we estimate the differential change in concentration of the basic form of the indicator $(I_1-I_2/I_1)$ at two $CO_2$ partial pressures (2.8% and 8.4% $CO_2$) which bracket the range of interest (for clinical monitoring of blood gases in this case). For the case of HPTS, $(I_1-I_2)/I_1$ corresponds to the change in fluorescence of a sensor when excited at 460 mm. For the purpose of this invention, it is recognized by those skilled in the art that $(I_1-I_2)/I_1$ can be related to measurements of other indicators where, for example, the acidic form of the indicator is measured, the ratio of acid and base forms of the indicator is monitored, the phase shift of the total emission is measured, etc. Our modeling program matches experimental measurements with the following accuracies (pH±0.02, osmolarities ±0.1%, and HPTS predominance ±1%).

Model for Sensor Drift

While we can estimate the amount of an impurity in a sensor by chemical analysis, the partitioning coefficients ($K_p$) of migratable impurities between the aqueous and silicone phases is not generally known. Therefore, the absolute concentrations of these impurities in the aqueous compartment is not known with certainty.

In our model, we assume an initial concentration of migratable impurity in the internal aqueous compartment at a particular pH. We also assume that the silicone is an infinite reservoir for accumulation of charge neutral acids or amines. With these assumptions, we estimate the change in concentration of aqueous impurities as a function of $CO_2$ partial pressure. This provides relative estimates of drift. The following discussion demonstrates these concepts for acetate induced drift.

At thermodynamic equilibrium, the concentration of a charge neutral acid is dictated by a pH dependent acid dissociation equilibrium and a silicone dependent acid partitioning equilibrium.

$$[CH_3OOH]_{aq} = [H^+][CH_3COO^-]/K_a \qquad \text{eq.6}$$

$$[CH_3OOH]_{aq} = K_p[CH_3OOH]_{silicone} \qquad \text{eq.7}$$

We define a thermodynamic reference point for the aqueous phase, for example 3.3 mF acetate at pH 9.0, for which the equations for charge balance (eq 1) and partitioning (eq. 7) are satisfied. This defines a value for the quantity $K_p[CH_3OOH]_{silicone}$ on the right side of equation 7. Next we allow the contaminated sensor to equilibrate with air. Acetic acid is allowed to migrate between the silicone and the aqueous phase until equations 1 and 7 are satisfied at this new pH. At this point point, we determine a calibration relationship for the air equilibrated sensor. Next we elevate the $CO_2$ partial pressure, to 6% for example. The pH drops substantially and the concentration of HPTS(base) is noted. Acetic acid is then allowed to migrate from the aqueous phase into the silicone until equations for charge balance (eq 1) and partitioning (eq. 7) are again satisfied. In the process, the buffering capacity of the aqueous compartment changes, the pH rises to a new value, and the concentration of HPTSCoase) increases. The $CO_2$ conditioning drift at 6% $CO_2$ is expressed in % mm drift (to equilibrium and not merely for a three hour period as described in FIG. 3b), using the calibration equation for the air equilibrated sensor.

Results from Modeling

Figure 10B:
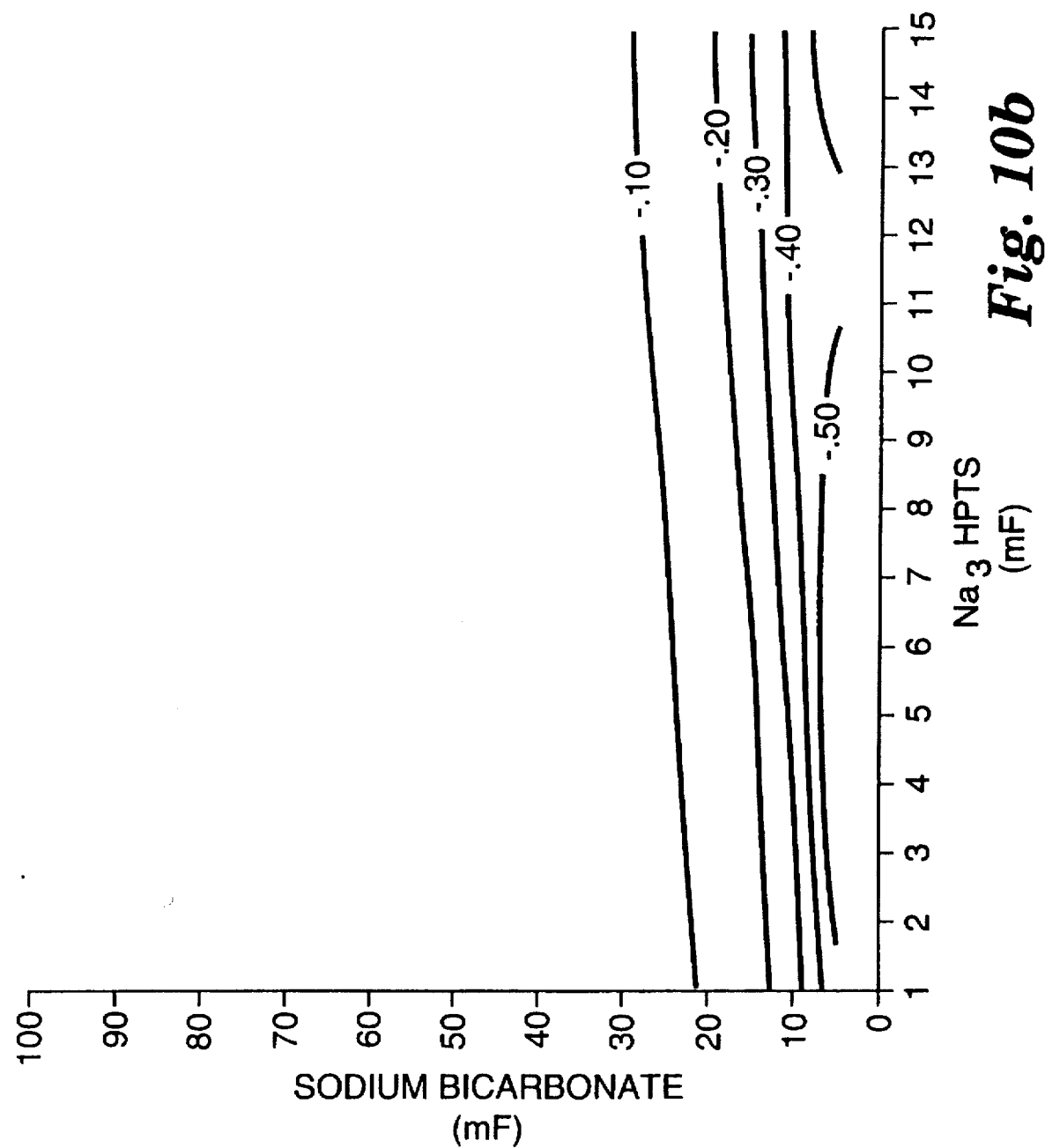

FIG. 10a shows the calculated response for several drift free $CO_2$ sensor formulations made with HPTS indicator and sodium bicarbonate buffer. The formal concentrations of $Na_3HPTS$ and $NaHCO_3$ are shown along the x and y axes, respectively. FIG. 10e shows the calculated response for several drift free $CO_2$ sensor formulations made with 10 mM HPTS indicator, sodium bicarbonate buffer and a mixture of dibasic and monobasic phosphate buffer. The sodium chloride concentration is maintained at 128 mM throughout this example. Migratible impurites are absent. Contours in FIGS. 10a and 10e represent aqueous formulations with the same value of the ratio $(I_1-I_2/I_1)$. For clinical applications, values of $(I_1-I_2/I_1)$ in the range of 0.2 to 0.5, and more preferably in the range of 0.30 to 0.40. This corresponds to formal sodium bicarbonate concentrations between 5 and 40 mM and more preferably between 10 and 20 mM.

Importantly, the pKa of the HPTS dye is dependent on ionic strength and is near 7.1 in FIG. 10a. By increasing the pKa of the indicator, the desired values of $(I_1-I_2/I_1)$ are achieved at higher formal concentrations of sodium bicarbonate. For example, by replacing the HPTS with carboxy SNARF-X (pKa=7.9), the desired values of $(I_1-I_2/I_1)$ are achieved using sodium bicarbonate concentrations between 25 to 200 mM and more preferably between 55 to 100 mM.

For sensors containing only amine impurities, $CO_2$ conditioning drift is reduced by using high concentrations of $NaHCO_3$. The desired values of $(I_1-I_2/I_1)$ are achieved by choosing an indicator with a correspondingly high pKa. FIG. 10b shows the % mm drift (when an air equilibrated sensor is moved into a medium equilibrated with 6 volume % COD calculated when the $NaHCO_3$ based sensors of FIG. 10a are contaminated with ammonia to a thermodynamic reference point of 3.0 mF aqueous ammonium at pH 7.0. FIG. 10f shows the % mm drift (when an air equilibrated sensor is moved into a medium equilibrated with 6 volume % $CO_2$ calculated when the mixed phosphate based sensors of FIG. 10e are contaminated with ammonia to a thermodynamic reference point of 3.0 mF aqueous ammonium at pH 7.0. For both FIGS. 10b and 10f the % mm drift is reduced from over 25% to less than 6% by increasing the $NaHCO_3$ concentration from 10 mM to greater than 40 mM. $CO_2$ conditioning drift is reduced because the operating range of the sensor is more basic and more of the amine impurity remains in the silicone.

Table 9a shows the decline in amine induced drift as the concentration of sodium bicarbonate is increased from 15 to 32 to 78 mM. A desired sensitivity of $(I_1-I_2)/I_1=0.32-0.36$ is achieved through appropriate choice of indicator pKa, in this case HPTS, Dextran SNAFL-2, and carboxy SNARF-X, respectively. Attachment of SNAFL-2 to the dextran not only modifies the pKa but also prevents possible migration of the dye from the aqueous phase into the silicone. Note that for all three of the bicarbonate based sensors in Table 9a, the change in pH (air→ 6% $CO_2$) remains near 2 pH units. The decline in amine induced drift at higher bicarbonate concentrations is principally due to the increase in the operating pH, not a decrease in ApH. The higher operating pH drives more of the amine into the silicone at all $CO_2$ partial pressures thereby reducing the amount of amine involved in partitioning.

For sensors containing only acid impurities, $CO_2$ conditioning drift is reduced by using lower concentrations of $NaHCO_3$. The desired values of $(I_1-I_2/I_1)$ are achieved by choosing an indicator with a correspondingly low pKa. In this case, drift free performance is achieved by using buffer compositions that are prepared from low concentrations of $NaHCO_3$ (5–15 mM) and elevated concentrations of the indicator and/or a phosphate buffer, introduced as a 50:50 mixture of $NaH_2PO_4$ and $Na_2HPO_4$. FIG. 10c shows the % mm drift (when an air equilibrated sensor is moved into a medium equilibrated with 6 volume % $CO_2$) calculated when the NaHCO, based sensors of FIG. 10a are contaminated with acetic acid to a thermodynamic reference point of 3.3 mF aqueous acetate at pH 9.0. The % mm drift is reduced from over 20% to less than 6% by decreasing the NaHCO, concentration from 20 mM to less than 10 mM at an HPTS concentration of 10 mM. However, at a lower concentration of HPTS (e.g., 2 mM) improved performance cannot be achieved. Drift is reduced at the 10 mM HPTS concentration because the HPTS serves as a buffer to limit the pH change on going from air equilibrated medium to 6% $CO_2$. Added phosphate buffer can have the same effect in reducing acid induced drift. FIG. 10g shows the % mm drift (when an air equilibrated sensor is moved into a medium equilibrated with 6 volume % $CO_2$) calculated when the mixed phosphate based sensors of FIG. 10e are contaminated with acetic acid to a thermodynamic reference point of 3.3 mF aqueous acetate at pH 9.0. The % mm drift is reduced below 6% by decreasing the $NaHCO_3$ concentration below 15 mM at an HPTS concentration of 10 mM and a mixed phosphate buffer concentration of 10 mM.

Figure 10D:
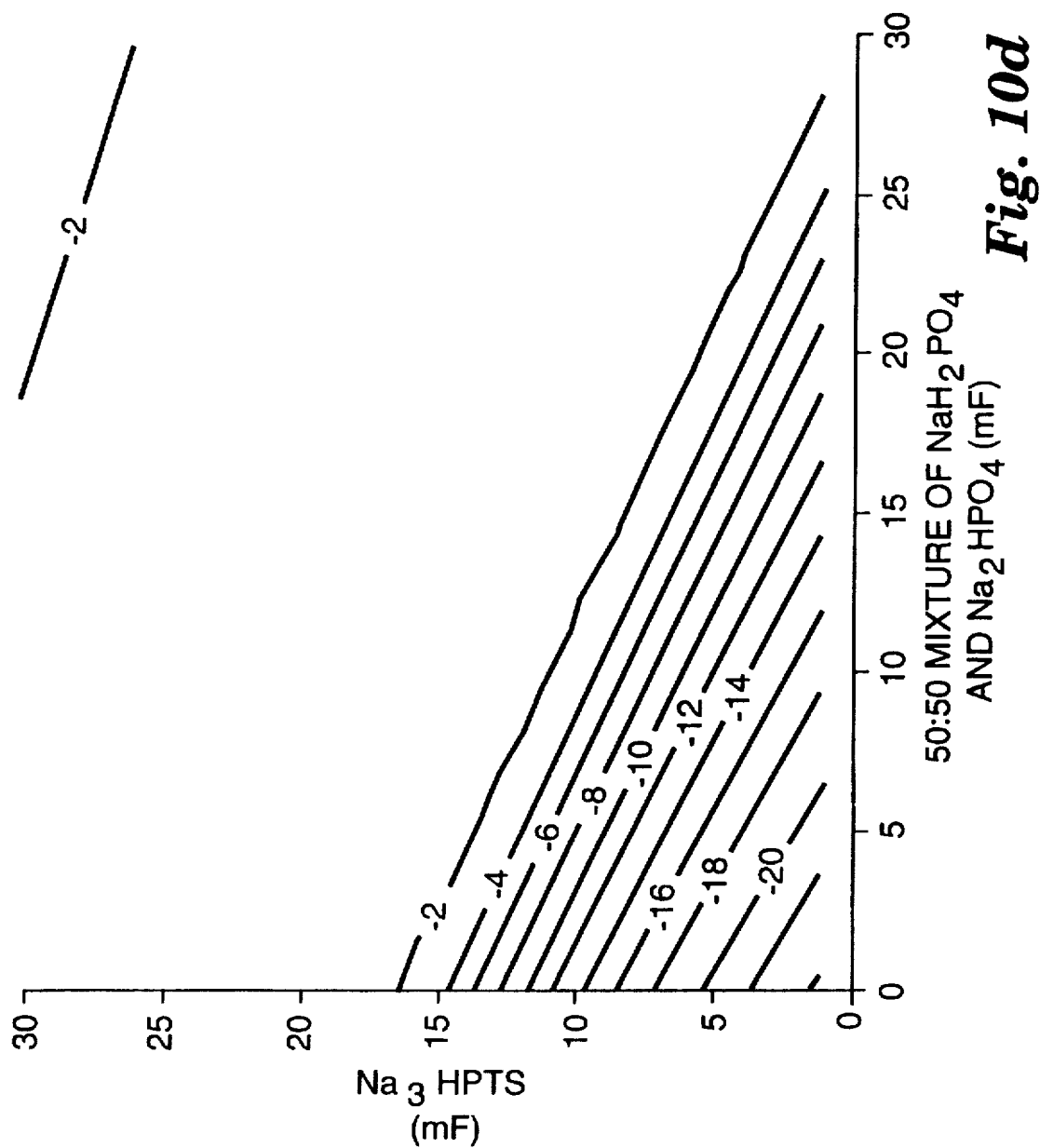
Figure 10E:
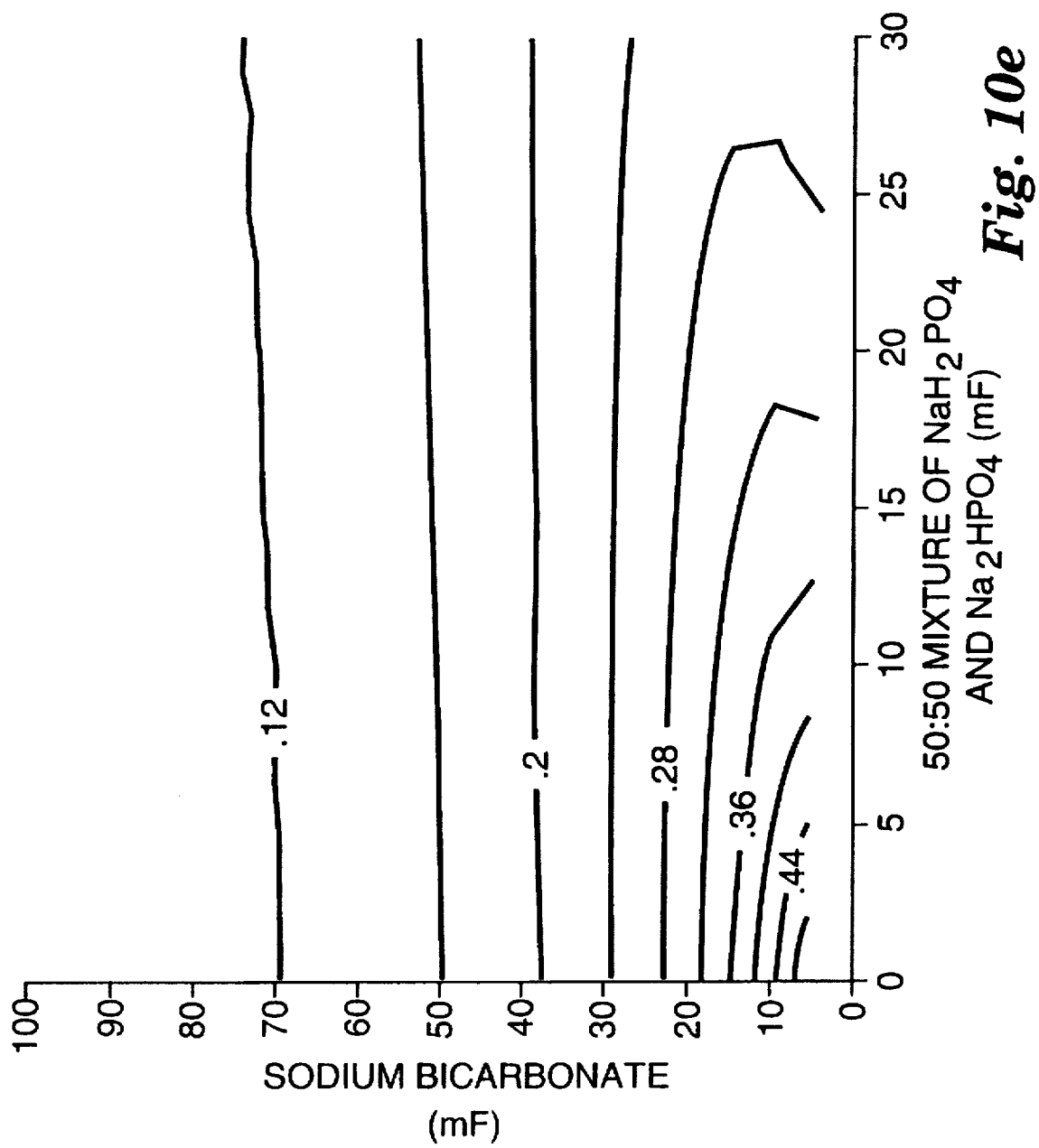
Figure 10F:
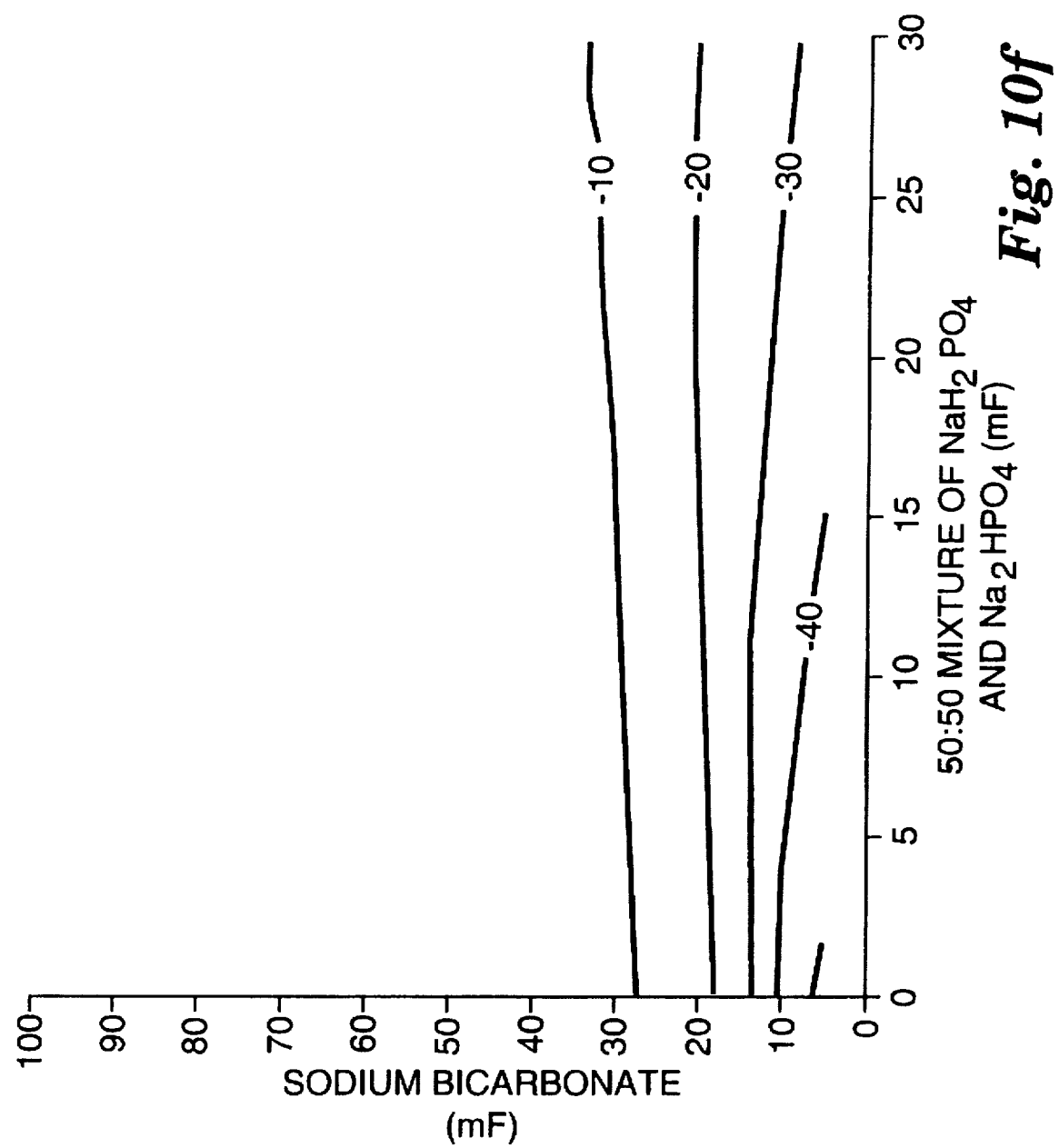
Figure 10G:
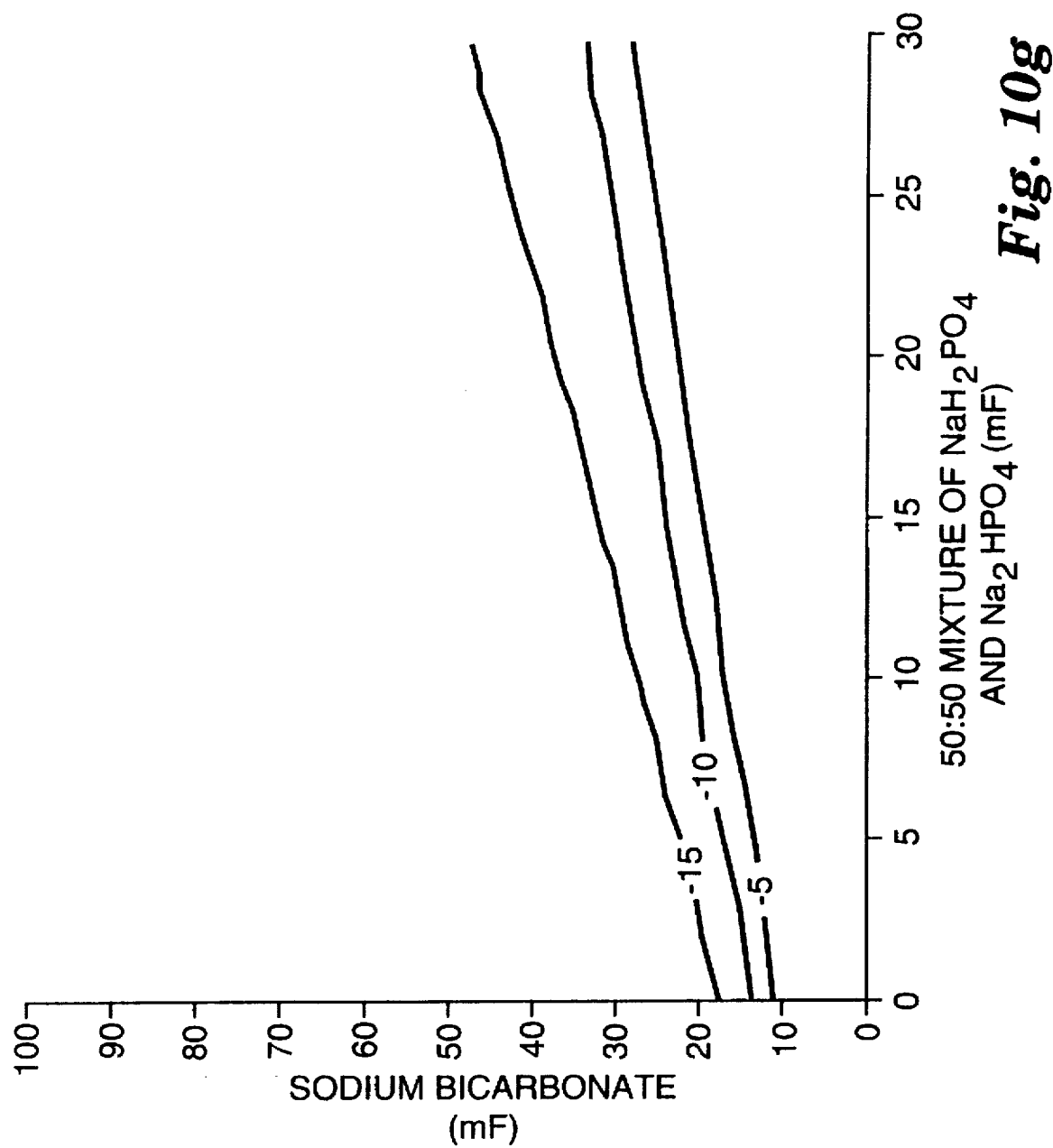

FIG. 10d shows the % mm drift (when an air equilibrated sensor is moved into a medium equilibrated with 6 volume % $CO_2$) calculated for sensors having buffer compositions prepared from 15 mM $NaHCO_3$ and various amounts of HPTS and a 50:50 mixture of $NaH_2PO_4$ and $Na_2HPO_4$ and contaminated with acetic acid to a thermodynamic reference point of 3.3 mF aqueous acetate at pH 9.0.

In the absence of phosphate buffer, drift is reduced from 20% to less than 4% as the HPTS concentration is increased from 5 to 15 mM. Also, at an HPTS concentration of 10 mM, the drift decreases from 13% to less than 4% as the mixed phosphate concentration is increased from 0 to 10 mM. More generally, as the ratio $$\frac{[HPTS] + [Phos]/2}{[NaHCO_3]}$$

goes from 0.33 to 1.0 the drift decreases from 20% to less than 4%. Preferably, the sum of the molar concentration of the indicator component and one-half of the molar concentration of the mixture of phosphate salts divided by the molar concentration of the bicarbonate salt is at least 0.66.

Table 9b shows the extent of acid induced drift for HPTS based sensor designed to have sensitivities between $(I_1-I_2)/I_1=0.32-0.36$. All sensors have aqueous phases prepared from 15 mM $NaHCO_3$ and various amounts of HPTS indicator and the mixed phosphate buffer. For sensors prepared with 5 mM HPTS indicator, the drift decreases from 20% to less than 4% as the mixed phosphate concentration is increased from 0 to 25 mM. Note that the reduction in drift is due to a decrease in $\Delta pH$ (air→6%) for the more highly buffered sensors.

When there is a mixture of both acid and amine impurities, drift is significant at all concentrations of $NaHCO_3$. At low $NaHCO_3$, drift is dominated by amines. At high $NaHCO_3$, drift is dominated by acids. If the amount of the acid and amine impurities is not too large, a buffer with intermediate properties can be used to reduce the drift. In this case, drift-free performance is achieved by using buffer compositions that are prepared from higher concentrations of $NaHCO_3$ (to reduce amine induced drift) and elevated concentrations of indicator and/or phosphate buffer (to reduce acid induced drift). Here we use a carbonate/phosphate mixed buffer system to substantially reduce the pH change between air and 6% $CO_2$.

FIG. 10e shows the calculated sensitivity $(I_1-I_2/I_1)$ for $CO_2$ sensor formulations prepared with 10 mM HPTS indicator and various amounts of $NaHCO_3$ and mixed phosphate buffer. Again, the sodium chloride concentration is 128 mM. Migratible impurites are absent. Contours represent aqueous formulations with the same value of $(I_1-I_2/I_1)$.

In this case, drift free sensors can be prepared using aqueous phase compositions having $NaHCO_3$ concentrations greater than 20 mF (and preferably greater than 40 mF) and having concentrations of HPTS and mixed phosphate buffer which satisfy the condition that $$\frac{[HPTS] + [Phos]/2}{[NaHCO_3]}$$

is greater than 0.6, more preferably greater than 0.8 and most preferably greater than 1.0 the indicator is chosen such that the pKa provides sensitivity of $(I_1-I_2)/I_1$ between 0.2 and 0.5 and more preferably between 0.3 and 0.4.

For sensors prepared as described in Run #17 of Table 2a (run 5 of Table 9c), both acetic acid and ammonia impurities were present. Drift was greater than 16%/hr. Table 9c shows that the drift can be reduced by employing aqueous phase compositions in which the concentration of HPTS is increased and a mixed phosphate buffer is added.

Buffer compositions used in runs 1, 2 and 4 of Table 9c all have the same susceptibility to amine induced drift and a decreasing susceptibility to acid induced drift. This indicates that acid induced drift has been substantially eliminated and that amine induced drift is principally responsible for the remaining 4–5% of drift.

TABLE 9a

| Indicator | pKa | [NaHCO$_3$] | Drift | pH$_{air}$ | pH$_{6\%}$ | $\Delta pH$ |
|---|---|---|---|---|---|---|
| HPTS | 7.05 | 15 | −26 | 9.24 | 7.16 | 2.08 |
| Dextran SNAFL-2 | 7.5 | 32 | −5 | 9.47 | 7.49 | 1.98 |
| Carboxy SNARF-X | 7.9 | 78 | −3 | 9.70 | 7.86 | 1.84 |

TABLE 9b

| Phosphate | HPTS | Drift | pH$_{air}$ | pH$_{6\%}$ | $\Delta pH$ |
|---|---|---|---|---|---|
| 0 | 5 | −20 | 9.11 | 7.08 | 2.03 |
| 0 | 10 | −13 | 8.85 | 6.98 | 1.87 |
| 0 | 15 | −3 | 8.15 | 6.88 | 1.27 |
| 5 | 5 | −17 | 9.01 | 7.05 | 1.96 |
| 15 | 5 | −7 | 8.63 | 7.00 | 1.63 |
| 25 | 5 | −2 | 7.76 | 6.96 | 0.8 |

TABLE 9c

| Run | HPTS | Na$_2$CO$_3$ | Na$_3$PO$_4$ | Na$_2$HPO$_4$ | Drift (5/hr) |
|---|---|---|---|---|---|
| 1 | 10 | 10 | — | — | 4.2 |
| 2 | 10 | — | 10 | — | 4.4 |
| 3 | 10 | — | 5 | 5 | 3.7 |
| 4 | 10 | — | 20 | — | 4.6 |
| 5 | 6.36 | 6.6 | — | — | 16.5 |

Example 10

Following the procedure of Example 1, Run 1, a sensor was tested for its response time. A similar sensor, but containing 1.0 mM HPTS, 8 mM Na$_2$CO$_3$ and 144 mM CaCl, was also prepared and tested. The sensor of Example 1, Run 1 had a response time of 120 seconds when moved from air to 4.9% CO$_2$. The other sensor had a response time of 42 seconds when moved from air to 4.9% CO$_2$. Both sensors were substantially drift free.

Various modifications and alterations of this invention will be apparent to those skilled in the art without departing from the scope and spirit of this invention, and it should be understood that this invention is not limited to the illustrative embodiments set forth herein.

What is claimed is:

1. A sensor for measuring the concentration of an analyte in a medium comprising:

a sensing element comprising a sensing composition having an aqueous first phase comprising a pH sensitive indicator component in a buffer solution, wherein said buffer solution comprises less than 100 mM of a bicarbonate ion, wherein the concentration of said pH sensitive indicator component in said sensing composition is effective to provide a signal in response to the concentration of carbon dioxide in a medium to which said sensing composition is exposed, said carbon dioxide being effective to alter the pH of said aqueous phase, and a hydrophobic second phase which is permeable to said analyte and impermeable to ionized hydrogen, wherein said aqueous phase is dispersed within said hydrophobic phase, and wherein said sensing composition is substantially free of partitioning species, other than the analyte of interest, which migrate between said phases in response to a change in pH in said aqueous phase or between the sensing composition and the medium and which migration substantially affects said concentration dependent signal;

an excitation assembly positioned and adapted to provide an excitation signal to said sensing element;

a detector assembly positioned and adapted to detect an emitted signal from said sensing element, said sensing element being capable of providing said emitted signal in response to being exposed to said excitation signal; and a processor assembly positioned and adapted to analyze said emitted signal in determining the concentration of said analyte in said medium.

2. A sensor according to claim 1, wherein said sensing composition, immediately after being equilibrated in a first medium having a $pCO_2$ of 0.25 mmHg, provides a measurement of $CO_2$ partial pressure which drifts less than 6% over a three hour period when moved from said first medium to a second medium having a $pCO_2$ of 45.6 mmHg.

3. A sensor according to claim 1, wherein said pH sensitive indicator component is present in said aqueous phase between a concentration of 2 and 10 mM and is selected from the group consisting of 2',7'-bis-(2-carboxyethyl)-5-(and-6)-carboxyfluorescein; 5-(and -6)-carboxy-2', 7'-dichlorofluorescein; 5-(and -6)-carboxy-4',5'-dimethylfluorescein; carboxy5'(and 6')-carboxy-3,10-dihydroxy-spiro[7H-benzo[c]xanthene-7,1'(3'H)-isobenzofuran]-3'-one; carboxy5'(and 6')-carboxy-9-chloro-3,10-dihydroxy-spiro[7H-benzo[c]xanthene-7,1'(3'H)-isobenzofuran]-3'-one; carboxy5'(and 6')-carboxy-10-dimethylamino-3-hydroxy-spiro[7H-benzo[c]xanthene-7,1'(3'H)-isobenzofuran]-3'-one; carboxy5'(and 6')-carboxy-10-diethylamino-3-hydroxy-spiro[7H-benzo[c]xanthene-7,1'(3'H)-isobenzofuran]-3'-one; carboxy5'(and 6')-carboxy-3-hydroxy-tetrahydroquinolizino[1,9-hi]spiro[7H-benzo[c]xanthene-7,1'(3'H)-isobenzofuran]-3'-one; 4-chloromethyl-7-hydroxycoumarin; 4-[2-chloro-6-(ethylamino)-7-methyl-3-oxo-3H-xanthen-9-yl]-1,3-benzene-dicarboxylic acid; dextran, 2',7'-bis(2-carboxyethyl)-5(and 6)-carboxy-fluorescein, anionic; dextran, 4-[2-chloro-6-(ethylamino)-7-methyl-3-oxo-3H-xanthen-9-yl]-1,3-benzene-dicarboxylic acid, anionic; dextran, 7-hydroxycoumarin, neutral; dextran, b-methylumbelliferone, neutral; dextran, 9-chloro-3,10-dihydroxy-spiro[7H-benzo[c]xanthene-7,1'(3'H)-isobenzofuran]-3'-one, anionic; dextran, 10-dimethylamino-3-hydroxy-spiro[7H-benzo[c]xanthene-7,1'(3'H)-isobenzofuran]-3'-one, anionic; 8-hydroxypyrene-1,3,6-trisulfonic acid, trisodium salt; and 3,10-dihydroxy-spiro[7H-benzo[c]xanthene-7,1'(3'H)-isobenzofuran]-3-one.

4. A sensor according to claim 1, wherein said aqueous phase further comprises a emulsification enhancement agent selected from the group consisting of poly(ethylene oxide), poly(ethylene glycol), poly(acrylamide), poly(dimethylacrylamide), poly(vinylmethyl acetomide), poly(styrene sulfonate), poly(vinylalcohol), poly(vinylpyrollidone), poly(hydroxyethylacrylate), poly(hydroxymethylacrylate), poly(acrylic acid), poly(vinyl methyl ether), dextran, hydroxyethylcellulose, hydroxypropyl cellulose, carboxymethylcellulose, methylcellulose, hydroxypropyl(methylcellulose), hydroxybutyl(methylcellulose), xanthan gum, guar gum, alginic acid, and carageenen, wherein said agent is present in an concentration between 1 and 50 weight percent based on the total aqueous phase components, and wherein said sensor comprises less than 3 mM of acidic or basic partitioning species, based on the volume of said aqueous phase, throughout the operating range of the sensor.

5. A sensor according to claim 1, wherein said sensor comprises less than 1 mM of an acidic partitioning species, based on the volume of said aqueous phase, throughout the operating range of the sensor.

6. A sensor according to claim 1, wherein said sensor comprises less than 1 mM of a basic partitioning species, based on the volume of said aqueous phase, throughout the operating range of the sensor.

7. A sensor for measuring the concentration of an analyte in a medium comprising:

a sensing element comprising a sensing composition having an aqueous first phase comprising a pH sensitive indicator component, wherein the concentration of said pH sensitive indicator component in said sensing composition is effective to provide a signal in response to the concentration of carbon dioxide in a medium to which said sensing composition is exposed, said carbon dioxide being effective to alter the pH of said aqueous phase, and a hydrophobic second phase which is permeable to said analyte and impermeable to ionized hydrogen, wherein said aqueous phase is dispersed within said hydrophobic phase, and wherein said sensing composition comprises less than 1 mM of acidic or basic partitioning species, other than the analyte of interest, which migrate between said phases in response to a change in pH in said aqueous phase or between the sensing composition and the medium and which migration substantially affects said concentration dependent signal;

an excitation assembly positioned and adapted to provide an excitation signal to said sensing element;

a detector assembly positioned and adapted to detect an emitted signal from said sensing element, said sensing element being capable of providing said emitted signal in response to being exposed to said excitation signal; and a processor assembly positioned and adapted to analyze said emitted signal in determining the concentration of said analyte in said medium.

8. A sensor according to claim 7, wherein said aqueous phase comprises a buffer solution equivalent in composition to a solution prepared with up to 100 mM of a bicarbonate salt, and wherein said sensing composition, immediately after being equilibrated in a first medium having a $pCO_2$ of 0.25 mmHg, provides a measurement of $CO_2$ partial pressure which drifts less than 3% over a three hour period when moved from said first medium to a second medium having a $pCO_2$ of 45.6 mmHg.

9. A sensor for measuring the concentration of an analyte in a medium comprising:

a sensing element comprising a sensing composition having an aqueous first phase comprising between an effective amount and 20 mM of a pH sensitive indicator component in a buffer solution, wherein said buffer solution has a buffering capacity equivalent to a solution prepared with between 20 and 100 mM of a bicarbonate salt and up to 50 mM of a 50:50 mixture of a monobasic and dibasic phosphate salt, wherein said pH sensitive indicator component is effective to provide a signal in response to the concentration of carbon dioxide in a medium to which said sensing composition is exposed, said carbon dioxide being effective to alter the pH of said aqueous phase, and a hydrophobic second phase which is permeable to said analyte and impermeable to ionized hydrogen, wherein said aqueous phase is dispersed within said hydrophobic phase, wherein said sensing composition is substantially free of acidic partitioning species, other than the analyte of interest, which migrate between said phases in response to a change in pH in said aqueous phase or between the sensing composition and the medium and which migration substantially affects said concentration dependent signal, wherein said sensing composition, immediately after being equilibrated in a first medium having a $pCO_2$ of 0.25 mmHg, provides a measurement of $CO_2$ partial pressure which drifts less than 12% over a three hour period when moved from said first medium to a second medium having a $pCO_2$ of 45.6 mmHg, and wherein said sensing composition has a specific sensitivity bwtween 0.2 and 0.5;

an excitation assembly positioned and adapted to provide an excitation signal to said sensing element;

a detector assembly positioned and adapted to detect an emitted signal from said sensing element, said sensing element being capable of providing said emitted signal in response to being exposed to said excitation signal; and a processor assembly positioned and adapted to analyze said emitted signal in determining the concentration of said analyte in said medium.

10. A sensor according to claim 9, wherein said buffer solution is equivalent in composition to a solution prepared with between 40 and 80 mM of a bicarbonate salt.

11. A sensor according to claim 9, wherein said sensor comprises less than 1 mM of an acidic partitioning species and less than 3 mM of a basic partitioning species, based on the volume of said aqueous phase, throughout the operating range of the sensor, and wherein said analyte is carbon dioxide, said indicator component is a salt hydroxypyrene trisulfonic acid, and said hydrophobic phase comprises silicone.

12. A sensor for measuring the concentration of an analyte in a medium comprising:

a sensing element comprising a sensing composition having an aqueous first phase comprising between an effective amount and 20 mM of a pH sensitive indicator component in a buffer solution, wherein said buffer solution has a buffering capacity equivalent to a solution prepared with at least 20 mM of a bicarbonate salt and up to 50 mM of a 50:50 mixture of a monobasic and dibasic phosphate salt, wherein said pH sensitive indicator component is effective to provide a signal in response to the concentration of carbon dioxide in a medium to which said sensing composition is exposed, said carbon dioxide being effective to alter the pH of said aqueous phase, and a hydrophobic second phase which is permeable to said analyte and impermeable to ionized hydrogen, wherein said aqueous phase is dispersed within said hydrophobic phase, wherein said sensing composition is substantially free of acidic partitioning species, other than the analyte of interest, which migrate between said phases in response to a change in pH in said aqueous phase or between the sensing composition and the medium and which migration substantially affects said concentration dependent signal, wherein said sensing composition, immediately after being equilibrated in a first medium having a $pCO_2$ of 0.25 mmHg, provides a measurement of $CO_2$ partial pressure which drifts less than 12% over a three hour period when moved from said first medium to a second medium having a $pCO_2$ of 45.6 mmHg, wherein said sensing composition has a specific sensitivity between 0.2 and 0.5, and wherein said aqueous phase does not include the combination of hydroxypyrene trisulfonic acid and polyvinylpyrolidone;

an excitation assembly positioned and adapted to provide an excitation signal to said sensing element;

a detector assembly positioned and adapted to detect an emitted signal from said sensing element, said sensing element being capable of providing said emitted signal in response to being exposed to said excitation signal; and a processor assembly positioned and adapted to analyze said emitted signal in determining the concentration of said analyte in said medium.

13. A sensor according to claim 12, wherein said sensing composition, immediately after being equilibrated in a first medium having a $pCO_2$ of 0.25 mmHg, provides a measurement of $CO_2$ partial pressure which drifts less than 3% over a three hour period when moved from said first medium to a second medium having a $pCO_2$ of 45.6 mmHg, and wherein said buffer solution is equivalent in composition to a solution prepared with at least 50 mM of a bicarbonate salt.

14. A sensor according to claim 12, wherein said sensor comprises less than 1 mM of an acidic partitioning species and less than 3 mM of a basic partitioning species, based on the volume of said aqueous phase, throughout the operating range of the sensor, and wherein said analyte is carbon dioxide, said indicator component is a salt of hydroxypyrene trisulfonic acid, and said hydrophobic phase comprises silicone.

15. A sensor for measuring the concentration of an analyte in a medium comprising:

a sensing element comprising a sensing composition having an aqueous first phase comprising a pH sensitive indicator component in a buffer solution, wherein said buffer solution has a buffering capacity equivalent to a solution prepared with at least one of a bicarbonate salt and a 50:50 mixture of a monobasic phosphate salt and a dibasic phosphate salt, wherein the sum of the molar concentration of the indicator component and one-half of the molar concentration of the mixture of phosphate salts divided by the molar concentration of the bicarbonate salt is at least 0.66, wherein said pH sensitive indicator component is effective to provide a signal in response to the concentration of carbon dioxide in a medium to which said sensing composition is exposed, said carbon dioxide being effective to alter the pH of said aqueous phase, and a hydrophobic second phase which is permeable to said analyte and impermeable to ionized hydrogen, wherein said aqueous phase is dispersed within said hydrophobic phase, wherein said sensing composition is substantially free of basic partitioning species, other than the analyte of interest, which migrate between said phases in response to a change in pH in said aqueous phase or between the sensing composition and the medium and which migration substantially affects said concentration dependent signal, wherein said sensing composition, immediately after being equilibrated in a first medium having a $pCO_2$ of 0.25 mmHg, provides a measurement of $CO_2$ partial pressure which drifts less than 12% over a three hour period when moved from said first medium to a second medium having a $pCO_2$ of 45.6 mmHg, and wherein said sensing composition has a specific sensitivity between 0.2 and 0.5;

an excitation assembly positioned and adapted to provide an excitation signal to said sensing element;

a detector assembly positioned and adapted to detect an emitted signal from said sensing element, said sensing element being capable of providing said emitted signal in response to being exposed to said excitation signal; and a processor assembly positioned and adapted to analyze said emitted signal in determining the concentration of said analyte in said medium.

16. A sensor according to claim 15, wherein said sensor comprises less than 3 mM of an acidic partitioning species and less than 1 mM of a basic partitioning species, based on the volume of said aqueous phase, throughout the operating range of the sensor, and wherein said sensing composition, immediately after being equilibrated in a first medium having a $pCO_2$ of 0.25 mmHg, provides a measurement of $CO_2$ partial pressure which drifts less than 6% over a three hour period when moved from said first medium to a second medium having a $pCO_2$ of 45.6 mmHg.

17. A sensor according to claim 15, wherein said analyte is carbon dioxide, said indicator component is a salt of hydroxypyrene trisulfonic acid, and said hydrophobic phase comprises silicone, and wherein said sensor comprises less than 1 mM of an acidic partitioning species and less than 0.5 mM of a basic partitioning species, based on the volume of said aqueous phase, throughout the operating range of the sensor.

18. A sensor according to claims 1, 9, or 15, wherein said sensor is of such a size as to be capable of being intravenously introduced into the body of a patient.

19. A sensor according to claims 7, 9, or 15, wherein said sensor further comprises a cassette comprising a flow through housing.

20. A sensor for measuring the concentration of an analyte in a medium comprising:

a sensing element comprising a sensing composition having an aqueous first phase comprising a pH sensitive indicator component in a buffer solution, wherein said buffer solution has a buffering capacity equivalent to a solution prepared with at least 15 mM of a bicarbonate salt and up to 50 mM of a 50:50 mixture of a monobasic and dibasic phosphate salt, wherein the ratio of the sum of the molar concentration of the indicator component and one-half of the molar concentration of the mixture of phosphate salts divided by the molar concentration of the bicarbonate salt is at least 0.66, wherein said pH sensitive indicator component is effective to provide a signal in response to the concentration of carbon dioxide in a medium to which said sensing composition is exposed, said carbon dioxide being effective to alter the pH of said aqueous phase, and a hydrophobic second phase which is permeable to said analyte and impermeable to ionized hydrogen, wherein said aqueous phase is dispersed within said hydrophobic phase, wherein said sensing composition, immediately after being equilibrated in a first medium having a $pCO_2$ of 0.25 mmHg, provides a measurement of $CO_2$ partial pressure which drifts less than 12% over a three hour period when moved from said first medium to a second medium having a $pCO_2$ of 45.6 mmHg, and wherein said sensing composition has a specific sensitivity between 0.2 and 0.5;

an excitation assembly positioned and adapted to provide an excitation signal to said sensing element;

a detector assembly positioned and adapted to detect an emitted signal from said sensing element, said sensing element being capable of providing said emitted signal in response to being exposed to said excitation signal; and a processor assembly positioned and adapted to analyze said emitted signal in determining the concentration of said analyte in said medium.

21. A sensor according to claim 20, wherein said buffer solution ratio is at least 1, and wherein said sensing composition, immediately after being equilibrated in a first medium having a $pCO_2$ of 0.25 mmHg, provides a measurement of $CO_2$ partial pressure which drifts less than 6% over a three hour period when moved from said first medium to a second medium having a $pCO_2$ of 45.6 mmHg.

22. A sensor according to claims 1, 12, or 20, wherein said sensor has a response time less than 1 minute.

23. A sensor according to claims 7, 12, or 20, wherein said sensor is maintained in an air-equilibrated buffer prior to temporal physiological sampling.

24. A sensor according to claim 12, 15, or 20, wherein said sensor further comprises an optical fiber.

* * * * *

UNITED STATES PATENT AND TRADEMARK OFFICE
CERTIFICATE OF CORRECTION

PATENT NO.: 5,607,645

DATED: March 4, 1997

INVENTOR(S): James G. Bentsen and Kenneth B. Wood

It is certified that error appears in the above-identified patent and that said Letters Patent is hereby corrected as shown below:

Col. 8, line 36, insert after "two" -- $CO_2$ --.

Col. 12, line 46, "00,000" should read -- 10,000 --.

Col. 15, line 51, "irapermeability" should read -- impermeability --.

Col. 16, line 27, "(=94 949-aliphatic)" should read – ($\sigma$–aliphatic) --.

Col. 22, line 56, "carded" should read -- carried --.

Col. 23, line 46, "Coming" should read -- Corning --.

Col. 24, line 21, "convened" should read -- converted --.

Col. 28, line 65, "Coming" should read -- Corning --.

Col. 29, line 63, "CO:" should read -- $CO_2$ --.

Col. 37, line 32, "HPTSCoase" should read -- HPTS(base) --.

Col. 38, line 28, "ApH" should read -- $\Delta$pH --.

Signed and Sealed this

First Day of June, 1999

Attest:

Attesting Officer

Q. TODD DICKINSON

Acting Commissioner of Patents and Trademarks